US007319086B1

(12) United States Patent
Collyer et al.

(10) Patent No.: US 7,319,086 B1
(45) Date of Patent: Jan. 15, 2008

(54) METHOD OF PROPHYLAXIS AND TREATMENT AND AGENTS USEFUL FOR SAME

(75) Inventors: Charles Andrew Collyer, Glebe (AU); Neil Hunter, Pennant Hills (AU); Arthur Anthony De Carlo, Jr., Birmingham, AL (US)

(73) Assignee: University of Sydney, New South Wales (AU)

( * ) Notice: Subject to any disclaimer, the term of this patent is extended or adjusted under 35 U.S.C. 154(b) by 0 days.

(21) Appl. No.: 09/980,370

(22) PCT Filed: May 26, 2000

(86) PCT No.: PCT/AU00/00599

§ 371 (c)(1),
(2), (4) Date: May 17, 2002

(87) PCT Pub. No.: WO00/72875

PCT Pub. Date: Dec. 7, 2000

(30) Foreign Application Priority Data

May 28, 1999 (AT) .................................. PQ0652

(51) Int. Cl.
*A61K 38/00* (2006.01)
*G01N 33/53* (2006.01)

(52) U.S. Cl. .......................................... 514/2; 435/7.1
(58) Field of Classification Search ............. 424/9.362; 530/385, 350; 540/145; 435/141, 7.1; 514/12, 514/649, 220
See application file for complete search history.

(56) References Cited

FOREIGN PATENT DOCUMENTS

WO    WO 96/17936    *  6/1996
WO    WO 97/34629    *  9/1997

OTHER PUBLICATIONS

Bramanti et al. J. Bacteriology, V175, N22, Nov. 1993, pp. 7413-7420.*
Aduse-Opoku et al. (1997). "The Tla Protein of *Porphyromonas gingivalis* W50: A Homolog of the RI Protease Precursor (PrpRI) Is an Outer Membrane Receptor Required for Growth on Low Levels of Hemin," *J. Bacteriol.* 179(15):4778-4788.
Albandar et al. (1997). "Putative Periodontal Pathogens in Subgingival Plaque of Young Adults With and Without Early-Onset Periodontitis," *J. Periodontol* 68:973-981.
Altschul et al. (1990). "Basic Local Alignment Search Tool," *J. Mol. Biol.* 215:403-410.
Altschul et al. (1997). "Gapped BLAST and PSI-BLAST: A New Generation of Protein Database Search Programs," *Nucl. Acids Res.* 25(17):3389-3402.
Argos, P. (1987). "A Sensitive Procedure to Compare Amino Acid Sequences," *J. Mol. Biol.* 193:385-396.

Beck et al. (1998). "Periodontitis: A Risk Factor for Coronary Heart Disease," *Ann. Periodontol* 3(1):127-141.
Bedi, G.S. and T. Williams. (1994). "Purification and Characterization of a Collagen-Degrading Protease from *Porphyromanas gingivalis,*" *J. Biol. Chem.* 269(1):599-606.
Bonner W.M. and R.A. Laskey. (1974). "A Film Detection Method for Tritium-Labelled Proteins and Nucleic Acids in Polyacrylamide Gels," *Eur. J. Biochem.* 46:83-88.
Calkins et al. (1998). "Inactivation of Tumor Necrosis Factor-α by Proteinases (Gingipains) from the Periodontal Pathogen, *Porphyromanas gingivalis,*" *J. Biol. Chem.* 273(12):6611-6614.
DeCarlo, A.A. and G.J. Harber. (1997). "Hemagglutinin Activity and Heterogeneity of Related *Porphyromanas gingivalis* Proteinases," *Oral Microbiol. Immunol.* 12:47-56.
DeCarlo et al. (1997). "Activation and Novel Processing of Matrix Metalloproteinases by a Thiol-Proteinase from the Oral Anaerobe *Porphyromanas gingivalis,*" *J. Dent. Res.* 76(6):1260-1270.
DeCarlo et al. (1998). "Induction of Matrix Metalloproteinases and a Collagen-Degrading Phenotype in Fibroblasts and Epithelial Cells by Secreted *Porphyromanas gingivalis* Proteinase," *J. Periodontol Res.* 33:408-420.
DeCarlo et al. (1999). "Porphyrin-Mediated Binding to Hemoglobin by the HA2 Domain of Cysteine Proteinases (Gingipains) and Hemagglutinins from the Periodontol Pathogen *Porphyromanas gingivalis,*" *J. Bact.* 181(12):3784-3791.
Dzink et al. (1988). "The Predominant Cultivable Microbiota of Active and Inactive Lesions of Destructive Periodontal Diseases," *J. Clin. Periodontol* 15:316-323.

(Continued)

*Primary Examiner*—Robert Mondesi
(74) *Attorney, Agent, or Firm*—Morrison & Foerster LLP

(57) ABSTRACT

The present invention relates generally to a method for the prophylaxis and treatment of infection by microorganisms in biological environments from where the microorganisms acquire iron, heme or porphyrin, generally but not exclusively for growth. Particular biological environments contemplated by the present invention include but are not limited to vascular regions and cavities as well as mucosal membranes in animals including mammals, reptiles, amphibians and fish and in avian species as well as hooves of livestock animals. The method of the present invention involves interrupting, reducing or otherwise antagonizing the interaction between a microbial-derived polypeptide, such as but not limited to a polypeptide having cysteine proteinase activity, and a porphyrin-containing molecule in such as heme. The present invention further provides agents useful in the prophylaxis and treatment of microbial infection of biological environments such as vascular regions and cavities including mucosal membranes as well as hooves involving microbial acquisition of iron, heme or porphyrin. Such agents are particularly useful as components in therapeutic compositions. Particularly important microbial infections targeted by the present invention involve infections in the oral cavity, nasopharynx, oropharynx, vagina and urethra in mammals such as humans. Other important microbial infections including infections of hooves in livestock animals such as sheep, cattle and goats.

18 Claims, 35 Drawing Sheets

OTHER PUBLICATIONS

Eke et al. (1989). "Cytotoxic Activity of Crude Extracts of *Bacteroides gingivalis*," *J. Med. Microb.* 28:5-8.

Eley, B.M. and S.W. Cox. (1996) "Correlation Between Gingivian/Gingipain and Bacterial Dipeptidyl Peptidase Activity in Gingival Crevicular Fluid and Periodontol Attachment Loss in Chronic Periodontitis Patients. A 2-Year Longitudianl Study,". *J. Periodontol* 67:703-716.

Evans et al. (1992). "Peridontopathic Potential of Two Strains of *Porphyromanas gingivalis* in Gnotobiotic Rats," *Arch. Oral Biol.* 37(10):813-819.

Fiehn et al. (1992). Periodontal Bone Loss in *Porphyromanas gingivalis*-Infected Specific Pathogen-Free Rats After Preinoculation with Endogenous *Streptococcus sanguis J. Periodontol Res.* 27:609-614.

Fishburn et al. (1991). "Degradation of Plasma Proteins by the Trypsin-Like Enzyme of *Porphyromanas gingivalis* and Inhibition of Protease Activity by a Serine Protease Inhibitor of Human Plasma," *Oral Microbiol. Immunol.* 6:209-215.

Fletcher et al. (1997). Interactions Between Periodontopathogenic Bacteria and Cytokines, *J. Periodontol Res.* 32:200-205.

Fujimura, S. and T. Nakamura. (1989). "Multiple Forms of Proteases of *Bacteroides gingivalis* and Their Cellular Location," *Oral Microbiol. Immunol.* 4:227-229.

Grenier, D. and D. Mayrand. (1987). "Functional Characterization of Extracellular Vesicles Produced by *Bacteroides gingivalis*," *Infect. Immun.* 55(1):111-117.

Haffajee, A.D. and S.S Socransky. (1994). "Microbial Etiological Agents of Destructive Periodontal Diseases," *Periodontology 2000* 5:78-111.

Hanazawa et al. (1985). "Functional Role of Interleukin 1 in Periodontal Disease: Induction of Interleukin 1 Production by *Bacteroides gingivalis* Lipopolysaccharide in Peritoneal Macrophages from C3H/HeN and C3H/HeJ Mice," *Infect. Immun.* 50(1):262-270.

Hanazawa et al. (1991). "*Bacteroides (Porphyromonas) gingivalis* Fimbriae Activate Mouse Peritoneal Macrophages and Induce Gene Expression and Production of Interleukin-1," *Infect. Immun.* 59(6):1972-1977.

Holt et al. (1988). "Implantation of *Bacteroides gingivalis* in Nonhuman Primates Initiates Progression of Periodontitis," *Science* 239:55-57.

Imamura et al. (1994). Pathogenesis of Periodontitis: A Major Arginine-Specific Cysteine Proteinase from *Porphyromanas gingivalis* Induces Vascular Permeability Enhancement through Activation of the Kallikrein/Kinin Pathway, *J. Clin. Invest.* 94:361-367.

Imamura et al. (1997). "Activation of Blood Coagulation Factor X by Arginine-Specific Cysteine Proteinases (Gingipain-Rs) from *Porphyromanas gingivalis*," *J. Biol Chem.* 272(25):16062-16067.

Laemmli, U.K. (1970). "Cleavage of Structural Proteins During the Assembly of the Head of Bacteriophage T4," *Nature* 227:680-685.

Lantz et al. (1991). "Identification of *Porphyromanas gingivalis* Components that Mediate its Interactions with Fibronectin," *J. Bacteriol.* 173(14):4263-4270.

Larjava et al. (1987). "Fibronectin Fragmentation Induced by Dental Plaque and *Bacteroides gingivalis*," *Scand. J. Dent. Res.* 95:308-314.

Malek et al. (1994). "Inactivation of the *Porphyromanas gingivalis fimA* Gene Blocks Periodontal Damage in Gnotobiotic Rats," *J. Bacteriol.* 176:1052-1059.

Marmur J. and P. Doty. (1962). "Determination of the Base Composition of Deoxyribonucleic Acid from its Thermal Denaturation Temperature," *J. Mol. Biol.* 5:109-118.

McDermid et al. (1988). "Effect of Environmental pH on Enzyme Activity and Growth of *Bacteroides gingivalis* W50," *Infect. Immun.* 56(5):1096-1100.

Mikolajczyk-Pawlinska et al. (1998). "Genetic Variation of *Porphyromanas gingivalis* Genes Encoding Gingipains, Cysteine Proteinases with Arginine or Lysine Specificity," *Biol. Chem.* 379:205-211.

Nakayama et al. (1998). "Haemoglobin Receptor Protein is Intragenically Encoded by the Cysteine Proteinase-Encoding Genes and the Haemagglutinin-Encoding Gene of *Porphyromanas gingivalis*," *Mol. Microbiol.* 27(1):51-61.

Needleman S.B. and C.D. Wunsch (1970). "A General Method Applicable to the Search for Similarities in the Amino Acid Sequence of Two Proteins," *J. Mol. Biol.* 48:443-453.

Nishikata, M. and F. Yoshimura. (1991). "Characterization of *Porphyromanas (Bacteroides) gingivalis* Hemagglutinin as a Protease," *Biochem. Biophys. Res. Comm.* 178(1):336-342.

Norris, J.M. and D.N. Love. (1995). "Serum Responses of Cats with Periodontal/Gingival Disease to Members of the Genus *Porphyromanas*," *Clin. Infect. Dis.* 20(Suppl. 2):314-316.

Okamoto et al. (1998). "Involvement of a Lysine-Specific Cysteine Proteinase in Hemoglobin Adsorption and Heme Accumulation by *Porphyromanas gingivalis*," *J. Biol. Chem.* 273(33):21225-21231.

Page, R.C. (1998). "The Pathobiology of Periodontal Diseases May Affect Systemic Diseases: Inversion of a Paradigm," *Ann. Periodontol* 3:108-120.

Pike et al. (1994). "Lysine- and Arginine-Specific Proteinases from *Porphyromanas gingivalis*," *J. Biol. Chem.* 269(1):406-411.

Potempa et al. (1995). "The Multiple Forms of Trypsin-like Activity Present in Various Strains of *Porphyromanas gingivalis* Are Due to the Presence of either Arg-Gingipain of Lys-Gingipain," *Infect. Immun.* 63(4):1176-1182.

Qui et al. (1996). "Identification and Characterization of a C(K/R)TC Motif as a Common Epitope Present in All Subtypes of Hepatitis B Surface Antigen," *J. Immunol.* 156:3350-3356.

Rangarajan et al. (1997). "The *prpR1* and *prR2* Arginine-Specific Protease Genes of *Porphyromanas gingivalis* W50 Produce Five Biochemically Distinct Enzymes," *Mol. Microbiol.* 23(5):955-965.

Sato et al. (1987). "Degradation of Human Secretory Immunoglobulin a by Protease Isolated from the Anaerobic Periodontopathogenic Bacterium, *Bacteroides gingivalis*," *Arch. Oral Biol.* 32(4):235-238.

Scott et al. (1993). "Purification and Characterization of a Potent 70-kDa Thiol Lysyl-Proteinase (Lys-Gingivain) from *Porphyromanas gingivalis* that Cleaves Kininogens and Fibrinogen," *J. Biol. Chem.* 268(11):7935-7942.

Shah, H.N. and S.E. Gharbia. (1989). "Lysis of Erythrocytes by the Secreted Cysteine Proteinase of *Porphyromanas gingivalis* W83," *FEMS Microbiol. Lett.* 61:213-218.

Shi et al. (1999). "Genetic Analyses of Proteolysis, Hemoglobin Binding, and Hemagglutination of *Porphyromanas gingavilis*," *J. Biol. Chem.* 274(25):17955-17960.

Sismey-Durrant, H.J. and R.M. Hopp. (1991). "Effect of Lipopolysaccharide from *Porphyromanas gingivalis* on Prostaglandin $E_2$ and Interleukin-1β Release from Rat Periosteal and Human Gingival Fibroblasts In Vitro," *Oral Microbiol. Immunol.* 6:378-380.

Slakeski et al. (1998). "Characterization of a Second Cell-Associated Arg-Specific Cysteine Proteinase of *Porphyromanas gingivalis* and Identification of and Adhesin-Binding Motif Involved in Association of the prtR and prtK Proteinases and Adhesins into Large Complexes," *Microbiology* 144:1583-1592.

Smalley et al. (1998). "The Periodontopathogen *Porphyromanas gingivalis* Binds Iron Protoporphyrin IX in the μ-oxo Dimeric Form: An Oxidative Buffer and Possible Pathogenic Mechanism," *Biochem J.* 331:681-685.

Sorsa et al. (1992). "Identification of Proteases from Periodontopathogenic Bacteria as Activators of Latent Human Neutrophil and Fibroblast-Type Interstitial Collagenases," *Infect. Immun.* 60(11):4491-4495.

Sundqvist et al. (1988). "Generation and Degradation of the Complement Fragment C5a in Human Serum by *Bacteroides gingivalis*," *Oral Microbiol. Immunol.* 3:103-107.

Touw et al. (1982). "Butyrate: A Cytotoxin for Vero Cells Produced by *Bacteroides gingivalis* and *Bacteroides asaccharolyticus*," *Antonie Van Leeuwenhoek* 48:315-325.

Towbin et al. (1979). "Electrophoretic Transfer of Proteins from Polyacrylamide Gels to Nitrocellulose Sheets: Procedure and some Applications," *Proc. Natl. Acad. Sci. USA* 76(9):4350-4354.

Wingrove et al. (1992). "Activation of Complement Components C3 and C5 by a Cysteine Proteinase (Gingipain-I) from *Porphyromanas (Bacteroides) gingivalis*," *J. Biol. Chem.* 267(26):18902-18907.

Yun et al. (1999). "Modulation of Major Histocompatibility Complex Protein Expression by Human Gamma Interferon Mediated by Cysteine Proteinase-Adhesin Polyproteins of *Porphyromanas gingivalis*," *Infect. Immuno.* 67(6):2986-2995.

* cited by examiner

Protoporphy

Deuteroporphyrin IX 2,4 Dihydrochloride

Dipyrrole No. 1

Dipyrrole No. 2

Dipyrrole No. 3

SEQUENCE LISTING

```
<160> NUMBER OF SEQ ID NOS: 8

<210> SEQ ID NO 1
<211> LENGTH: 15
<212> TYPE: PRT
<213> ORGANISM: Porphyromonas gingivalis

<400> SEQUENCE: 1

Ala Leu Asn Pro Asp Asn Tyr Leu Ile Ser Lys Asp Val Thr Gly
 1               5                  10                  15
```

```
<210> SEQ ID NO 2
<211> LENGTH: 25
<212> TYPE: DNA
<213> ORGANISM: Artificial sequence
<220> FEATURE:
<223> OTHER INFORMATION: Synthetic construct

<400> SEQUENCE: 2
aacctgcagc gcgcagactt cacgg                                           25

<210> SEQ ID NO 3
<211> LENGTH: 28
<212> TYPE: DNA
<213> ORGANISM: Artificial sequence
<220> FEATURE:
<223> OTHER INFORMATION: Synthetic construct

<400> SEQUENCE: 3
ggaagccaat ggcgccaaaa gatctagt                                        28

<210> SEQ ID NO 4
<211> LENGTH: 20
<212> TYPE: PRT
<213> ORGANISM: Artificial sequence
<220> FEATURE:
<223> OTHER INFORMATION: Synthetic construct

<400> SEQUENCE: 4

Gly Glu Ala Pro Ala Glu Trp Thr Thr Ile Asp Ala Asp Gly Asp Gly
 1               5                  10                  15

Gln Gly Trp Leu
         20

<210> SEQ ID NO 5
<211> LENGTH: 402
<212> TYPE: DNA
<213> ORGANISM: Porphyromonas gingivalis
<220> FEATURE:
<221> NAME/KEY: CDS
<222> LOCATION: (1)...(402)

<400> SEQUENCE: 5 gca gac ttc acg gaa acg ttc gag tct tct act cat gga gag gca cca      48
Ala Asp Phe Thr Glu Thr Phe Glu Ser Ser Thr His Gly Glu Ala Pro
 1               5                  10                  15 gcg gaa tgg act act atc gat gcc gat ggc gat ggt gag ggt tgg ctc      96
Ala Glu Trp Thr Thr Ile Asp Ala Asp Gly Asp Gly Glu Gly Trp Leu
                20                  25                  30 tgt ctg tct tcc gga caa ttg gac tgg ctc aca gct cat ggc ggc acc     144
Cys Leu Ser Ser Gly Gln Leu Asp Trp Leu Thr Ala His Gly Gly Thr
             35                  40                  45 aac gta gta agc tct ttc tca tgg aat gga atg gct ttg aat cct gat     192
Asn Val Val Ser Ser Phe Ser Trp Asn Gly Met Ala Leu Asn Pro Asp
         50                  55                  60 aac tat ctc atc tca aag gat gtt aca ggc gca acg aag gta aag tac     240
Asn Tyr Leu Ile Ser Lys Asp Val Thr Gly Ala Thr Lys Val Lys Tyr
 65                  70                  75                  80 tac tat cca gtc aac gac ggt ttt ccc ggg gat cac tat gcg gtg atg     288
Tyr Tyr Pro Val Asn Asp Gly Phe Pro Gly Asp His Tyr Ala Val Met
                 85                  90                  95 atc tcc aag acg ggc acg aac gcc gga gac ttc acg gtt gtt ttc gaa     336
Ile Ser Lys Thr Gly Thr Asn Ala Gly Asp Phe Thr Val Val Phe Glu
            100                 105                 110
```

```
gaa acg cct aac gga ata aat aag ggc gga gca aga ttc ggt ctt tcc    384
Glu Thr Pro Asn Gly Ile Asn Lys Gly Gly Ala Arg Phe Gly Leu Ser
        115                 120                 125 acg gaa gcc aat ggc gcc                                            402
Thr Glu Ala Asn Gly Ala
    130
```

<210> SEQ ID NO 6
<211> LENGTH: 134
<212> TYPE: PRT
<213> ORGANISM: Porphyromonas gingivalis

<400> SEQUENCE: 6

```
Ala Asp Phe Thr Glu Thr Phe Glu Ser Ser Thr His Gly Glu Ala Pro
1               5                   10                  15

Ala Glu Trp Thr Thr Ile Asp Ala Asp Gly Asp Gly Glu Gly Trp Leu
            20                  25                  30

Cys Leu Ser Ser Gly Gln Leu Asp Trp Leu Thr Ala His Gly Gly Thr
        35                  40                  45

Asn Val Val Ser Ser Phe Ser Trp Asn Gly Met Ala Leu Asn Pro Asp
    50                  55                  60

Asn Tyr Leu Ile Ser Lys Asp Val Thr Gly Ala Thr Lys Val Lys Tyr
65                  70                  75                  80

Tyr Tyr Pro Val Asn Asp Gly Phe Pro Gly Asp His Tyr Ala Val Met
                85                  90                  95

Ile Ser Lys Thr Gly Thr Asn Ala Gly Asp Phe Thr Val Val Phe Glu
            100                 105                 110

Glu Thr Pro Asn Gly Ile Asn Lys Gly Gly Ala Arg Phe Gly Leu Ser
        115                 120                 125

Thr Glu Ala Asn Gly Ala
    130
```

<210> SEQ ID NO 7
<211> LENGTH: 63
<212> TYPE: DNA
<213> ORGANISM: Porphyromonas gingivalis
<220> FEATURE:
<221> NAME/KEY: CDS
<222> LOCATION: (1)...(63)

<400> SEQUENCE: 7

```
gct ttg aat cct gat aac tat ctc atc tca aag gat gtt aca ggc gca    48
Ala Leu Asn Pro Asp Asn Tyr Leu Ile Ser Lys Asp Val Thr Gly Ala
1               5                   10                  15 acg aag gta aag tac                                                63
Thr Lys Val Lys Tyr
            20
```

<210> SEQ ID NO 8
<211> LENGTH: 21
<212> TYPE: PRT
<213> ORGANISM: Porphyromonas gingivalis

<400> SEQUENCE: 8

```
Ala Leu Asn Pro Asp Asn Tyr Leu Ile Ser Lys Asp Val Thr Gly Ala
1               5                   10                  15

Thr Lys Val Lys Tyr
            20
```

METHOD OF PROPHYLAXIS AND TREATMENT AND AGENTS USEFUL FOR SAME

CROSS-REFERENCE TO RELATED APPLICATIONS

This application is the U.S. National Phase of PCT International Application No. PCT/AU00/00599, filed May 26, 2000, which claims priority to Australian Provisional Patent Application No. PQ 0652, filed May 28, 1999, the disclosures of each of which are incorporated herein by reference in their entirety.

FIELD OF THE INVENTION

The present invention relates generally to a method for the prophylaxis and treatment of infection by microorganisms in biological environments from where the microorganisms acquire iron, heme or porphyrin, generally but not exclusively for growth. Particular biological environments contemplated by the present invention include but are not limited to vascular regions and cavities as well as mucosal membranes in animals including mammals, reptiles, amphibians and fish and in avian species as well as hooves of livestock animals. The method of the present invention involves interrupting, reducing or otherwise antagonizing the interaction between a microbial-derived polypeptide, such as but not limited to a polypeptide having cysteine proteinase activity, and a porphyrin-containing molecule such as heme. The present invention further provides agents useful in the prophylaxis and treatment of microbial infection of biological environments such as vascular regions and cavities including mucosal membranes as well as hooves involving microbial acquisition of iron, heme or porphyrin. Such agents are particularly useful as components in therapeutic compositions. Particularly important microbial infections targeted by the present invention involve infections in the oral cavity, nasopharynx, oropharynx, vagina and urethra in mammals such as humans. Other important microbial infections include infections of hooves in livestock animals such as sheep, cattle and goats.

BACKGROUND OF THE INVENTION

Bibliographic details of the publications numerically referred to in this specification are collected at the end of the description.

Proteinases are enzymes which hydrolyse peptide bonds in peptides, polypeptides and proteins. One particular group of proteinases, the endopeptidases, cleave bonds within the peptide chain with varying degrees of specificity for particular amino acyl residues. An example of an endopeptidase is a serine proteinase which is characterized by a catalytically active serine residue in its active centre. Another example is a cysteine proteinase (sometimes referred to as a thiol proteinase) which has free —SH groups in its active centre.

There is increasing evidence for the potential importance of proteinases in microbial infection. This is particularly highlighted by the involvement of cysteine proteinases in periodontal disease pathology cased by the Gram negative microorganism, Porphyromonas gingivalis. This microorganism was formally known as Bacteroides sp.

Periodontal disease affects a majority of adults in varying degrees and is associated with significant systemic morbidity (1,1a) including dental infection and loss of teeth. Porphyromonas gingivalis is implicated as an important pathogen by its high incidence and relative levels in human disease (2,2a) and by its virulence in mono-infected animals (3,4). Virulence of P. gingivalis has been attributed to several components of the microorganism including fimbriae (5,6), short-chain volatile acids (7,8), lipopolysaccharide (9,10), collagenase activity (11,12) and non-collagenolytic cysteine proteinase activity (13,14,15).

Cysteine proteinases have a range of activities including affecting the remodelling of matrix proteins and disrupting the immune response by stimulating collagen-degrading activity of host cells (13,14,16), degrading fibronectin (17), inactivating interferon-$\alpha$ (19) and interleukins (18,20), interfering with the complement cascade (21,22) and degrading immunoglobulins (23,24). Furthermore, clotting and vascular permeability mechanisms may be disturbed (15,25,26), fibrinogen may be degraded (15,27) and erythrocytes agglutinated and lysed (28,29) by cysteine proteinase activity.

A number of P. gingivalis cysteine proteinases described in several reports have been demonstrated to be antigenically related (14,30,31) to the products of three related genes (32,33). Cysteine proteinases from P. gingivalis are generally referred to as gingipains. Two major gingipains, Arg-gingipain (RgpA [formerly Arg-gingipain-1 or RGPA]) and Lys-gingipain (Kgp [formerly KGP]) [32], prefer proteinaceous substrates with an arginine or lysine in the P1 position, respectively.

The gingipains are expressed on the outer membrane of P. gingivalis and may also be released with residues or as soluble proteins (34,35,36). It has been proposed that P. gingivalis binds to hemoglobin via the gingipains (38).

The catalytic domains of RgpA and Kgp constitute approximately one third of the translated protein product. C-terminal to the catalytic domain, there are the following four domains: HA1, HA2, HA3 and HA4 which are highly homologous between RgpA and Kgp. These non-catalytic COOH-terminal domains have previously been named hemagglutinin (HA) domains because at least one was thought to participate in hemagglutination (30). Because all of the domains of the gingipains are found together predominantly in loose, non-covalent associations with one another after hydrolytic separation (34,37), the gingipains appear to be multifunctional proteins for aggregating erythrocytes then lysing these cells to obtain hemoglobin for the acquisition of iron, heme and/or porphyrin.

P. gingivalis is implicated as a periodontal pathogen of central importance by its relative high levels of coincidence with periodontal disease (52,53) and by its virulence in mono-infected animals (54). Pathogenicity of this organism has been attributed to several components including short chain volatile acids and lipopolysaccharide and there is increasing evidence for the critical role of fimbriae and multi-domain proteinase-adhesion proteins, i.e. the gingipains. Indirect mechanisms are also important since these proteases can subvert the control of the inflammatory response by degrading host control proteins leading to a tissue-destructive process (55).

This fastidious Gram negative anaerobic bacterium has an essential requirement for exogenous porphyrin, i.e. it is a porphyrin auxotroph and lacks a number of enzymes normally involved in porphyrin synthesis, including: glutamyl-tRNA reductase, porphobilinogen synthase, porphobilinogen deaminase, uroporphyrinogen III cosynthase, uroporphyrinogen decarboxylase, coporphyrinogen III oxidase, HemM or uroporphyrinogen III methylase. Porphyrins are critical in the function of the cytochromes of this organism and, therefore, in electron transfer related to energy currency. It has been further proposed that iron porphyrins accumulated at the cell surface constitute an effective anti-oxidant shield (56) which could explain the relative resistance of the organism to hydrogen peroxide. Of note, the organism requires supplementation of porphyrin, even in complex growth media. Thus, iron-free protoporphyrin IX can replace the requirement for hemin in media containing sufficient inorganic iron.

In the environment of the periodontium, it is accepted that there would be only trace concentrations of free heme. Hence, the apparent preferred source of both iron and porphyrin would be hemoglobin. Bleeding is a diagnostic feature of gingival inflammation and P. gingivalis can be implicated, as it has been shown to be highly competitive in utilizing hemoglobin as a source of both porphyrin and iron.

The elucidation of the molecular and biochemical mechanisms involved in key regulatory pathways, such as pathways involving the acquisition of iron, heme and porphyrin, is paramount in developing strategies for the control of disease. The inventors have now determined the molecular mechanism of HA2 domain binding to porphyrin-containing molecules such as hemoglobin and in particular heme. The elucidation of the mechanisms underlying hemoglobin binding provides a means for the rational design of antagonists to prevent, reduce or otherwise retard the growth and maintenance of microorganisms which require exogenous iron, heme or porphyrin.

SUMMARY OF THE INVENTION

Nucleotide and amino acid sequences are referred to by a sequence identifier, i.e. SEQ ID NO:1, SEQ ID NO:2, etc. A sequence listing is provided after the claims.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

An aspect of the present invention contemplates a method for the prophylaxis or treatment of infection by a microorganism in a biological environment from where the microorganism acquires iron, heme or porphyrin, said method comprising administering to said environment an effective amount of an agent for a time and under conditions sufficient to antagonize the interaction between a molecule derived from said microorganism and having an HA2 domain and an HA2-binding motif on a porphyrin-containing molecule present in said biological environment.

Another aspect of the present invention provides a method for the prophylaxis or treatment of infection by a microorganism in a mammal from where the microorganism acquires iron, heme or porphyrin, said method comprising administering to said environment an effective amount of an agent for a time and under conditions sufficient to antagonize the interaction between a molecule derived from said microorganism and having an HA2 domain and an HA2-binding motif on a porphyrin-containing molecule such as but not limited to hemoglobin or a precursor form thereof or part thereof such as heme.

Still another aspect of the present invention provides a method for the prophylaxis or treatment of infection by a microorganism in a mammal, said microorganism being substantially incapable of synthesizing porphyrins said method comprising administering to said mammal an effective amount of an agent for a time and under conditions sufficient to antagonize the interaction between a molecule derived from said microorganism and having an HA2 domain and an HA2-binding motif on a porphyrin-containing molecule such as but not limited to hemoglobin or a precursor form thereof or part thereof such as heme.

Yet another aspect of the present invention contemplates a method for prophylaxis or treatment of periodontal, pulmonary, vaginal, urethral or hoof disease resulting from infection by P. gingivalis or related microorganism in a mammal, said method comprising administering to said mammal an effective amount of an agent for a time and under conditions sufficient to antagonize the interaction between a P. gingivalis-derived molecule having an HA2 domain and an HA2-binding motif on a porphyrin-containing molecule such as but not limited to hemoglobin or a precursor form thereof or part thereof such as heme.

Even still another aspect of the present invention contemplates a method for the prophylaxis or treatment of infection by a microorganism in a mammal, said microorganism substantially requiring exogenous iron, heme or porphyrin for growth or maintenance wherein said method comprises administering to said mammal an effective amount of an agent for a time and under conditions sufficient to antagonize the interaction between a molecule derived from said microorganism and having an HA2 domain and an HA2-binding moiety on a porphyrin-containing molecule such as but not limited to hemoglobin or a precursor form thereof or part thereof such as heme and wherein said HA2 domain comprises:

(i) an amino acid sequence substantially encoded by the nucleotide sequence set forth in SEQ ID NO:5 or a nucleotide sequence having at least about 40% similarity thereto or capable of hybridizing thereto under low stringency conditions; and/or (ii) an amino acid sequence substantially as set forth in SEQ ID NO:6 or an amino acid sequence having at least about 40% similarity thereto or at least about 20% identity after optimum alignment with the same sequence;

wherein said amino acid sequence is capable of interacting with an HA2-binding motif on a porphyrin-containing molecule such as but not limited to hemoglobin or a precursor form thereof or part thereof such as heme.

Even yet another aspect of the present invention provides a method for the prophylaxis or treatment of infection by a microorganism in a mammal, said microorganism substantially requiring exogenous iron, heme or porphyrin for growth or maintenance wherein said method comprises administering to said mammal an effective amount of an agent for a time and under conditions sufficient to antagonize the interaction between a molecule derived from said microorganism and having an HA2 domain and an HA2-binding moiety on a porphyrin-containing molecule such as but not limited to hemoglobin or a precursor form thereof or part thereof such as heme and wherein said HA2 domain comprises:

(i) an amino acid sequence substantially encoded by the nucleotide sequence set forth in SEQ ID NO:5 or a nucleotide sequence having at least about 40% similarity thereto or capable of hybridizing thereto under low stringency conditions; and/or (ii) an amino acid sequence substantially as set forth in SEQ ID NO:6 or an amino acid sequence having at least about 40% similarity thereto or at least about 20% identity after optimum alignment with the same sequence;

and wherein the HA2-binding motif comprises a moiety structurally or functionally homologous to substructure (Ia) of structure (I) below:

Another aspect of the present invention contemplates a method for the prophylaxis or treatment of *P. gingivalis* infection or infection by a related microorganism in a mammal, said method comprising administering to said mammal an effective amount of an agent for a time and under conditions sufficient to antagonize the interaction between a *P. gingivalis*-derived HA2-containing molecule and an HA2-binding motif on a porphyrin-containing molecule such as but not limited to hemoglobin or a precursor form thereof or part thereof such as heme.

Still another aspect of the present invention contemplates a method for the prophylaxis or treatment of *P. gingivalis* infection or infection by a related microorganism in a mammal, said method comprising administering to said mammal an effective amount of an agent for a time and under conditions sufficient to antagonize the interaction between a *P. gingivalis*-derived HA2-containing molecule comprising the amino acid sequence ALNPDNYLISKD-VTG SEQ ID NO:1 or ALNPDNYLISKDVTGATKVKY SEQ ID NO:8 or an amino acid sequence having at least 40% similarity to SEQ ID NO:1 or SEQ ID NO:8 at least about 20% identity after optimum alignment with same sequence or an amino acid sequence encoded by the nucleotide sequence SEQ ID NO:7 or a nucleotide sequence having at least 40% similarity thereto or a nucleotide sequence capable of hybridizing thereto under low stringency conditions and an HA2-binding motif comprising and including propionic acid groups or anionic or salt forms thereof such as but not limited to the region defined by substructure (Ic) in Formula (I) on a porphyrin-containing molecule such as but not limited to hemoglobin or a precursor form thereof or part thereof such as heme.

Yet another aspect of the present invention provides an agent capable of antagonizing interaction between an HA2-containing molecule and an HA2-binding motif on a porphyrin-containing molecule such as but not limited to hemoglobin or a precursor form thereof or part thereof such as heme.

Even still another aspect of the present invention provides an agent capable of antagonizing interaction between an HA2-containing molecule and an HA2-binding motif on a porphyrin-containing molecule, said agent comprising propionic groups in planar alignment with respect to the molecular structure of said agent.

Even yet another aspect of the present invention provides a composition such as therapeutic or vaccine composition comprising an agent as herein before described and one or more pharmaceutically acceptable carriers and/or diluents.

A summary of the sequence identifiers referred to in the subject specification follows.

SUMMARY OF SEQUENCE IDENTIFIERS

| Sequence | Sequence Identifer |
|---|---|
| Amino acid marked for HA2 binding (peptide #1) | SEQ ID NO:1 |
| Forward primer to amplify HA2 | SEQ ID NO:2 |
| Reverse primer to amplify HA2 | SEQ ID NO:3 |
| Amino acid sequence of peptide #2 | SEQ ID NO:4 |
| Nucleotide sequence encoding HA2 domain | SEQ ID NO:5 |
| Amino acid sequence of HA2 domain | SEQ ID NO:6 |
| Nucleotide sequence encoding SEQ ID NO:8 | SEQ ID NO:7 |
| Amino acid marked for HA2 binding (peptide #3) | SEQ ID NO:8 |

BRIEF DESCRIPTION OF THE FIGURES

FIGS. 8a, 8b and 8c are graphical representations showing expression of HA2-related immunoreactive hemoglobin-binding protein from *P. gingivalis*. Aliquots of *P. gingivalis* culture medium were removed daily during a period of 8 d and immediately separated into a cell pellet and culture supernatant then frozen until use. $OD^{660}$ and purity of the culture were measured daily. The cell pellets were dispersed evenly into 1 ml of $PBS/N_3$. (8a) and (8b): Arg- and Lys-specific proteinase activities, respectively, of the cell-free culture supernatant (squares) and cellular fraction (triangles) were measured as described. Measurements of the cellular fractions were normalized to culture densities ($OD^{660}$) recorded daily. (8c): The HA2 domain (1/243 dilution, open squares) and HA2 domain associated with hemoglobin-binding (1/81 dilution, solid squares) in culture supernatants were measured by ELISA and ligand binding assay, respectively, as described. In *P. gingivalis* whole cell fractions, the HA2 domain (1/243 dilution, open triangles) and HA2 domain associated with hemoglobin-binding (1/9 dilution, solid triangles) were measured by ELISA and ligand binding assay, respectively, as described. Measurements of the cell-associated fractions were normalized to culture densities ($OD^{660}$) recorded daily. Corresponding background immunoreactivity with a murine anti-human CD-19 IgG was subtracted from each measurement. Data are representative of two separate experiments in which patterns of expression were similar.

DETAILED DESCRIPTION OF THE PREFERRED EMBODIMENT

Figure 1:
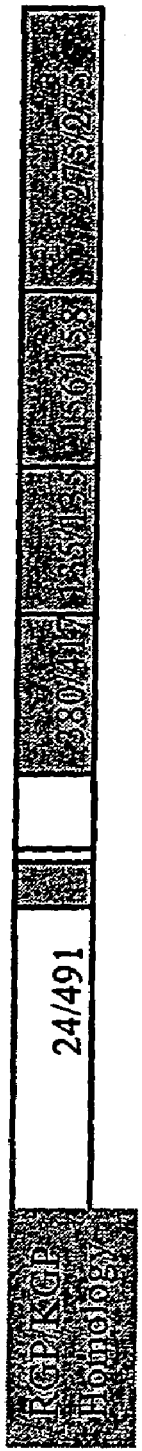
FIG. 1 is a diagrammatic representation of the domain structure and homologies between the gingipains, RgpA and Kgp. CAT represents putative catalytic domain and HA represents putative hemagglutinin domains. Shaded areas represent regions of >98% amino acid identity between the two gingipains. Fractions represent the degree of the identity for each RgpA domain.

One aspect of the present invention contemplates a method for the prophylaxis or treatment of infection by a microorganism in a biological environment from where the microorganism acquires iron, heme or porphyrin, said method comprising administering to said environment an effective amount of an agent for a time and under conditions sufficient to antagonize the interaction between a molecule derived from said microorganism and having an HA2 domain and an HA2-binding motif on a porphyrin-containing molecule present in said biological environment.

The term "biological environment" is used in its broadest context to include an environment comprising porphyrin-containing molecules. Particularly preferred porphyrin-containing molecules include hemoglobin and its precursors as well as heme. Preferably, the biological environment is a vascular region or cavity or a mucosal membrane in an animal species such as a mammal, reptile, amphibian, fish or bird or is a hoof of a livestock animal. More preferably, the animal is a mammal such as a human or livestock animal.

Accordingly, a preferred aspect of the present invention provides a method for the prophylaxis or treatment of infection by a microorganism in a mammal from where the microorganism acquires iron, heme or porphyrin, said method comprising administering to said environment an effective amount of an agent for a time and under conditions sufficient to antagonize the interaction between a molecule derived from said microorganism and having an HA2 domain and an HA2-binding motif on a porphyrin-containing molecule such as but not limited to hemoglobin or a precursor form thereof or part thereof such as heme.

Although the present invention is particularly directed to *P. gingivalis* infection in the oral cavity such as during periodontal disease, it extends to any disease condition resulting from microbial infection and in particular infection by *P. gingivalis* or a related microorganism involving the acquisition of iron, heme or porphyrin. Such microorganisms are required to acquire iron, heme or porphyrin as they do not possess a biosynthetic pathway for porphyrins. Examples of microorganisms related to *P. gingivalis* contemplated herein include but are not limited to *Salmonella* sp, *Serratia* sp, *Yersinia* sp, *Klebsiella* sp, *Vibrio* sp, *Pseudomas* sp, *E. coli*, *Haemophilus* sp and *Bordetella* sp. Examples of *P. gingivalis* or related microorganism infection contemplated by the present invention include infection of the oral cavity, nasopharynx, oropharynx, vagina and urethra as well as infection of mucosal membranes and infection of hooves of livestock animals such as sheep, cattle and goats. An "effective" amount means a porphyrin-binding interfering effective amount, i.e. an amount sufficient to interfere with HA2 domain interaction with a porphyrin moiety.

Another aspect of the present invention provides a method for the prophylaxis or treatment of infection by a microorganism in a mammal, said microorganism being substantially incapable of synthesizing porphyrins said method comprising administering to said mammal an effective amount of an agent for a time and under conditions sufficient to antagonize the interaction between a molecule derived from said microorganism and having an HA2 domain and an HA2-binding motif on a porphyrin-containing molecule such as but not limited to hemoglobin or a precursor form thereof or part thereof such as heme.

A related aspect of the present invention contemplates a method for prophylaxis or treatment of periodontal, pulmonary, vaginal, urethral or hoof disease resulting from infection by *P. gingivalis* or related microorganism in a mammal, said method comprising administering to said mammal an effective amount of an agent for a time and under conditions sufficient to antagonize the interaction between a *P. gingivalis*-derived molecule having an HA2 domain and an HA2-binding motif on a porphyrin-containing molecule such as but not limited to hemoglobin or a precursor form thereof or part thereof such as heme.

Reference herein to "*Porphyromonas gingivalis*" or its abbreviation "*P. gingivalis*" includes reference to all mutants, derivatives and variants of this organism as well as serological sub-types. The present invention further extends to microorganisms related to *P. gingivalis* at the metabolic, structural, biochemical, immunological and/or disease causing levels. Examples of related microorganisms are those listed above.

The term "HA2" domain is used in its broadest context and includes regions having structural or functional homology to the HA2 region. An HA2 domain comprises a sequence of amino acids having conformationally and/or linearly defined binding capacity to an HA2-binding motif on a porphyrin containing molecule such as hemoglobin and more particularly heme.

A particularly preferred HA2 domain comprises the following amino acid sequence:

Ala Asp Phe Thr Glu Thr Phe Glu Ser Ser Thr His Gly

Glu Ala Pro Ala Glu Trp Thr Thr Ile Asp Ala Asp Gly

Asp Gly Glu Gly Trp Leu Cys Leu Ser Ser Gly Gln Leu

Asp Trp Leu Thr Ala His Gly Gly Thr Asn Val Val Ser

Ser Phe Ser Trp Asn Gly Met Ala Leu Asn Pro Asp Asn

Tyr Leu Ile Ser Lys Asp Val Thr Gly Ala Thr Lys Val

Lys Tyr Tyr Tyr Pro Val Asn Asp Gly Phe Pro Gly Asp

His Tyr Ala Val Met Ile Ser Lys Thr Gly Thr Asn Ala

Gly Asp Phe Thr Val Val Phe Glu Glu Thr Pro Asn Gly

Ile Asn Lys Gly Gly Ala Arg Phe Gly Leu Ser Thr Glu

Ala Asn Gly Ala (SEQ ID NO:6)

or a sequence having at least about 40% similarity to at least about 10 contiguous amino acids thereof or at least about 20% identity after optimum alignment with the same sequence. Alternative percentage similarities include at least about 50% or 60% or 70% or 80% or 90% or above. Alternative percentage identities include at least about 25% or 30%, 40%, 50%, 60%, 70%, 80% or 90% or above. An HA2 domain is also conveniently defined by being encoded by a sequence of nucleotides comprising the following sequence:

gca gac ttc acg gaa acg ttc gag tct tct act cat gga gag gca cca gcg gaa tgg act act atc gat gcc gat ggc gat ggt gag ggt tgg ctc tgt ctg tct tcc gga caa ttg gac tgg ctc aca gct cat ggc ggc acc aac gta gta agc tct ttc tca tgg aat gga atg gct ttg aat cct gat aac tat ctc atc tca aag gat gtt aca ggc gca acg aag gta aag tac tac tat cca gtc aac gac ggt ttt ccc ggg gat cac tat gcg gtg atg atc tcc aag acg ggc acg aac gcc gga gac ttc acg gtt gtt ttc gaa gaa acg cct aac gga ata aat aag ggc gga gca aga ttc ggt ctt tcc acg gaa gcc aat ggc gcc (SEQ ID NO:5)

or a nucleotide sequence having at least 40% similarity to at least about 30 contiguous nucleotides thereof or a nucleotide sequence capable of hybridizing thereto under low stringency conditions. Alternative percentage similarities include at least about 50 or 60%, 70%, 80% or 90% or above.

Accordingly, another aspect of the present invention contemplates a method for the prophylaxis or treatment of infection by a microorganism in a mammal, said microorganism substantially requiring exogenous iron, heme or porphyrin for growth or maintenance wherein said method comprises administering to said mammal an effective amount of an agent for a time and under conditions sufficient to antagonize the interaction between a molecule derived from said microorganism and having an HA2 domain and an HA2-binding moiety on a porphyrin-containing molecule such as but not limited to hemoglobin or a precursor form thereof or part thereof such as heme and wherein said HA2 domain comprises:

(i) an amino acid sequence substantially encoded by the nucleotide sequence set forth in SEQ ID NO:5 or a nucleotide sequence having at least about 40% similarity thereto or capable of hybridizing thereto under low stringency conditions; and/or (ii) an amino acid sequence substantially as set forth in SEQ ID NO:6 or an amino acid sequence having at least about 40% similarity thereto or at least about 20% identity after optimum alignment with the same sequence;

wherein said amino acid sequence is capable of interacting with an HA2-binding motif on a porphyrin-containing molecule such as but not limited to hemoglobin or a precursor form thereof or part thereof such as heme.

Preferred molecules having an HA2 domain include cysteine proteinases such as gingipains, a product of the hagA gene and any TonB dependent protein carrying an HA2 domain and in particular those TonB dependent proteins involved in the acquisition of heme. An example of a TonB-dependent protein is Tla (TonB-linked adhesin) (44). The present invention, however, extends to all HA2-containing molecules.

The term "infection" is used in its most general sense and includes the presence or growth of P. gingivalis or related microorganism resulting in a disease condition or having the capacity to result in a disease condition. The term "infection" further encompasses P. gingivalis or related microorganism when present as part of the normal flora. Such bacteria may, under certain circumstances, be responsible for disease development. Prophylaxis is contemplated in accordance with the present invention to reduce the levels of P. gingivalis or related microorganism or to reduce the likelihood of a disease condition developing resulting from infection by P. gingivalis or a relative thereof.

The present invention is particularly directed to the treatment of P. gingivalis or a related microorganism in humans. The present invention extends, however, to the prophylaxis or treatment of P. gingivalis or related microorganisms in other mammals such as primates, livestock animals (e.g. sheep, cows, goats, pigs, horses, donkeys), companion animals (e.g. dogs, cats), laboratory test animals (e.g. mice, rats, guinea pigs, rabbits, hamsters) and captured wild animals.

In accordance with the present invention, it has been determined that the HA2 domain binds to a portion of the porphyrin moiety on a porphyrin-containing molecule such as but not limited to hemoglobin or a precursor form thereof or part thereof such as heme. Preferably, the HA2 domain interacts with a surface exposed heme moiety of hemoglobin.

In a particularly preferred embodiment, the HA2 region interacts with the region on porphyrin, and in particular heme, comprising exposed propionic groups or their anionic or salt forms.

A porphyrin molecule is considered to have the structure shown in (I):

wherein $R_1$ and $R_6$ are the same or different and each is an alkyl such as a methyl, ethyl or propyl group, or hydrogen, hydroxyl, carboxyl, aldehyde, acetaldehyde or keto group, M is a metal ion in various oxidation states such as but not limited to Fe, $Fe^{++}$ and $Fe^{+++}$ and is optionally present such that n is 0 or 1. A person skilled in the art will appreciate that when n is 0, the trivalency of the two $sp^3$ hybridized N atoms will be completed by a hydrogen atom.

It is proposed in accordance with the present invention that the HA2-binding motif comprises the molecule defined by structure (I). Preferably, the HA2-binding motif comprises the region in substructure (Ic). More preferably, the HA2-binding motif comprises the region in substructure (Ib). Even more preferably, the HA2-binding motif comprises the region defined by substructure (Ia). Reference herein to the "HA2-binding motif" includes and comprises the motif defined by substructure (Ic), preferably substructure (Ib) and more preferably substructure (Ia) or a structurally or functionally homologous region capable of interacting with the HA2 domain of a molecule such as but not limited to a cysteine proteinase.

Accordingly, another aspect of the present invention provides a method for the prophylaxis or treatment of infection by a microorganism in a mammal, said microorganism substantially requiring exogenous iron, heme or porphyrin for growth or maintenance wherein said method comprises administering to said mammal an effective amount of an agent for a time and under conditions sufficient to antagonize the interaction between a molecule derived from said microorganism and having an HA2 domain and an HA2-binding moiety on a porphyrin-containing molecule such as but not limited to hemoglobin or a precursor form thereof or part thereof such as heme and wherein said HA2 domain comprises:

(i) an amino acid sequence substantially encoded by the nucleotide sequence set forth in SEQ ID NO:5 or a nucleotide sequence having at least about 40% similarity thereto or capable of hybridizing thereto under low stringency conditions; and/or (ii) an amino acid sequence substantially as set forth in SEQ ID NO:6 or an amino acid sequence having at least about 40% similarity thereto or at least about 20% identity after optimum alignment with the same sequence;

and wherein the HA2-binding motif comprises a moiety structurally or functionally homologous to substructure (Ia) of structure (I) below:

(I)

(Ia)
(Ib)
(Ic)

wherein $R_1$ and $R_6$ are the same or different and each is an alkyl such as a methyl, ethyl or propyl group, or hydrogen, hydroxyl, carboxyl, aldehyde, acetaldehyde or keto group, M is a metal ion in various oxidation states such as but not limited to Fe, $Fe^{++}$ and $Fe^{+++}$ and is optionally present such that n is 0 or 1.

Preferably, the HA2-binding motif comprises substructure (Ib). More preferably, the HA2-binding molecule comprises substructure (Ia).

Another aspect of the present invention contemplates a method for the prophylaxis or treatment of P. gingivalis infection or infection by a related microorganism in a mammal, said method comprising administering to said mammal an effective amount of an agent for a time and under conditions sufficient to antagonize the interaction between a P. gingivalis-derived HA2-containing molecule and an HA2-binding motif on a porphyrin-containing molecule such as but not limited to hemoglobin or a pre cursor form thereof or part thereof such as heme.

Infection by P. gingivalis or related microorganism in accordance with this aspect of the present invention is one leading to or having the potential to lead to an infection of a mucosal or vascular region such in the oral cavity, nasopharynx, oropharynx, vagina or urethra as well as the hooves of farm animals.

Reference to a "P. gingivalis-derived HA2-containing molecule" includes gingipains bound to P. gingivalis as well as soluble forms of the cysteine proteinase and the hagA gene product as well as TonB-dependent proteins such as the Tla protein (44).

The term "antagonize" means and includes reducing, inhibiting or otherwise adversely affecting interaction between the HA2 domain and that part of the porphyrin ring and in particular heme which forms the HA2-binding motif on hemoglobin. The functional result of such antagonism is the inability or at least reduced capacity of P. gingivalis or related microorganism for acquiring iron, heme or porphyrin for use in, for example, metabolic pathways. Antagonizm may be complete, i.e. from about 90-100% or partial, i.e. from about 20 to about 90% as determined by binding assays or inhibition of P. gingivalis growth or maintenance.

Although not intending to limit the present invention to any one theory or mode of action, it is proposed that P. gingivalis and its relatives do not have a complete functional porphyrin-synthesizing pathway and hence are porphyrin auxotrophs. In particular, it is proposed that P. gingivalis lacks one or more of a glutamyl-t RNA reductase, porphobilinogen synthase, porphobilinogen deaminase, uroporphyrinogen III cosynthase, uroporphyrinogen decarboxylase, coproporphyrinogen III oxidase, HemM or uroporphyrinogen III methylase. As a result, P. gingivalis needs to acquire porphyrin for growth and/or maintenance or at least to facilitate growth and/or maintenance. Accordingly, by antagonizing the interaction between the HA2 domain and the HA2-binding motif the microorganism is unable to acquire porphyrin, iron or heme and infection can be controlled.

In one embodiment, the antagonism results from inhibiting interaction between a region of surface exposed porphyrin and in particular heme comprising propionic acid groups or their anionic or salt forms such as but not limited to the region defined by sub-structure (Ic) and an HA2 containing molecule comprising an epitope capable of interaction with monoclonal antibody mAb 5A1 (see ref 34). In accordance with the present invention, mAb 5A1 interacts with an epitope defined by amino acid sequence ALNPDNYLISKDVTG SEQ ID NO:1 or ALNPDNYLISKDVTGATKVKY SEQ ID NO:8 an amino acid sequence having at least 40% similarity thereto or at least about 20% identity after optimum alignment with same sequence including an amino acid sequence defined by SEQ ID NO:1 or SEQ ID NO:8 but which has single or multiple amino acid substitutions, deletions and/or additions.

In an alternative embodiment, the HA2 containing molecule does not contain the mAb5A1 epitope.

The amino acid sequence defined by SEQ ID NO:1 or SEQ ID NO:8 is not the porphyrin binding site but a useful marker for HA2.

Accordingly, another aspect of the present invention contemplates a method for the prophylaxis or treatment of P. gingivalis infection or infection by a related microorganism in a mammal, said method comprising administering to said mammal an effective amount of an agent for a time and under conditions sufficient to antagonize the interaction between a P. gingivalis-derived HA2-containing molecule comprising the amino acid sequence ALNPDNYLISKDVTG SEQ ID NO:1 or ALNPDNYLISKDVTGATKVKY SEQ ID NO:8 an amino acid sequence having at least 40% similarity to SEQ ID NO:1 or SEQ ID NO:8 or at least about 20% identity after optimum alignment with same sequence or an amino acid sequence encoded by the nucleotide sequence SEQ ID NO:7 or a nucleotide sequence having at least 40% similarity thereto or a nucleotide sequence capable of hybridizing thereto under low stringency conditions and an HA2-binding motif comprising and including propionic acid groups or anionic or salt forms thereof such as but not limited to the region defined by substructure (Ia) on a porphyrin-containing molecule such as but not limited to hemoglobin or a precursor form thereof or part thereof such as heme.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) (47). A detailed discussion of sequence analysis can be found in Unit 19.3 of Ausubel et al. (1998) (48).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to "similar" amino acids includes similarity at both the chemical and/or structural levels. Examples of similar amino acids based on chemical properties are as follows:—
non-polar—Gly, Leu, Pro, Val, Ala, Met, Trp, Phe, Ile
polar uncharged—Ser, Asn, Gln, Thr, Cys, Tyr
acidic—Asp, Glu
basic—His, Lys, Arg.

Examples of similar amino acids based on structural properties are as follows:—
Group 1—Asp, Asn, Glu, Gln, His
Group 2—Tyr, Phe, Trp
Group 3—Val, Pro, Cys, Ala, Thr, Ser, Gly
Group 4—Arg, Lys
Group 5—Met, Leu, Ile.

In essence, amino acids which are similar include those which are observed in related proteins to be substituted by their partners at a higher frequency of the particular amino acid substitution as compared with random mutation (58).

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (49). However, the $T_m$ of a duplex DNA decreases by 1° C. with every increase of 1% in the number of mismatch base pairs (50). Formamide is optional in these hybridization conditions. Accordingly, particularly preferred levels of stringency are defined as follows: low stringency is 6×SSC buffer [SSC comprises sodium chloride and sodium citrate; 20×SSC is prepared by dissolving 175.3 g of NaCl and 88.2 g of sodium citrate in 800 ml of $H_2O$; the pH is adjusted to 0.7 and the volume adjusted to 1 liter], 0.1% w/v sodium dodecyl sulphate (SDS) at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C. A salt is regarded as including any member of a class of compounds formed, together with water, by reaction of an acid with a base.

The identification of the molecular mechanism underlining HA2 interaction with hemoglobin provides a means for screening for antagonists of this interaction. Such antagonists are useful, for example, in the development of vaccines and therapeutic compositions for preventing or treating infection by P. gingivalis or related microorganisms.

Accordingly, another aspect of the present invention provides an agent capable of antagonizing interaction between an HA2-containing molecule and an HA2-binding motif on a porphyrin-containing molecule such as but not limited to hemoglobin or a precursor form thereof or part thereof such as heme.

Preferably, the agent antagonizes interaction between the HA2 containing molecule and a region on a porphyrin portion of hemoglobin comprising propionic acid groups or anionic or salt forms thereof.

Preferably, the region on hemoglobin is defined by substructure (Ic) as described above.

The agent may be a derivative of the HA2 containing molecule (e.g. gingipain or hagA gene product or Tla protein) or hemoglobin or may be identified following screening of a chemical library or following natural product screening. The latter includes screening of environments such as aquatic environments, coral, seabeds, microorganisms, plants and antarctic environments for naturally occurring molecules capable of acting as antagonists.

Alternatively, the HA2-containing molecule may be crystallized and antagonists derived based on the structure of the HA2 domain.

Any HA2-containing molecule such as the gingipain, hagA gene product or Tla protein or their derivatives may be used as vaccine components to generate antibodies to their HA2 domains or their immunological relatives. Alternatively, the antagonist may be an antibody to HA2 or an antibody to another region resulting in reduced binding of the HA2-containing molecule to hemoglobin. Antibodies may be employed from any source but may need to be humanized if the intended use is in humans unless the antibodies are topically applied. Alternatively, the antibodies are raised by lactating dairy animals to provide passive immunization, particularly in the form of secretory antibody in dairy products.

A range of potential antagonists may be identified from screening chemical libraries or specifically designed for chemical synthesis. For example, the present invention extends to structural analogues of porphyrin or porphyrin-like molecules. In one embodiment, a nitrogen may replace any carbon especially in the Ic portion of the molecule. Alternatively, a molecule may be prepared as a dimer or trimer minimizing a porphyrin or porphyrin-like molecule. The multimerization may, for example, be complexing with a metal group. All such structural analogues may act as antagonists for HA2 interaction.

Furthermore, HA2-interaction antagonists may also be identified from a family of HA2-like molecules. In general, in addition to molecules having amino acid sequence similarity or identity, a family of proteins may be identified which have a tertiary structure which enables that molecule to interact with an HA2 domain in a manner analogous or functionally related to known ligands of the HA2 domain. Proteins having a tertiary structure may differ at the amino acid identity level by up to 20%. Molecules may also be designed which retain tertiary functionality but differ at the amino acid level. Such molecules may be made by observing regions of the molecule which have a higher frequency of an amino acid substitution as compared with a random mutation. These particular substitutions may involve replacement by chemically related amino acids in the sequence such as a hydrophobic amino acid for a hydrophobic amino acid or a basic amino acid for a basic amino acid. Generally, such substitutions would result with an amino acid similarity having a homology greater than four standard deviations above the control mean (57).

The antagonists, therefore, may be peptides, polypeptides, proteins, antibodies, small or large chemical entities or combinations thereof and may be in isolated, naturally occurring form or may be in recombinant or chemically synthetic form.

Screening for antagonists may be accomplished in any number of ways. In one method, preparations of gingipains or HA2-containing parts thereof are incubated with potential antagonists and then subjected to chromatography or gel electrophoresis or immunoassay to screen for the formation of a complex.

In one particularly useful method, incubation mixtures of HA2-containing molecules and potential antagonists are spotted onto porous chromatography paper and allowed to migrate through a portion previously impregnated with an antibody to the HA2. The aim of this method is to identify HA2-containing molecule-antagonist combinations which can no longer bind to the antibody. Identification of HA2-containing molecules whose migration is not retarded provides for a potential antagonist for binding to a porphyrin-containing molecule such as but not limited to hemoglobin or a precursor form thereof or part thereof such as heme. Antibody mAb 5A1 may be used where more conformational antagonists are sought in the general HA2 region.

In addition to screening for suitable antagonists, the present invention enables the chemical synthesis and/or rational design for developing antagonists of HA2-porphyrin interaction. In particular, data presented herein indicates that planarity of the propionic face of the porphyrin molecule is important for effective binding to HA2. The rational design of antagonists requires, therefore, developing a molecule in which the propionic face is aligned in a plane with respect to the molecule to which the propionic face forms part. Molecules and in particular antagonists with such conformation are encompassed by the present invention.

Accordingly, another aspect of the present invention provides an agent capable of antagonizing interaction between an HA2-containing molecule and an HA2-binding motif on a porphyrin-containing molecule, said agent comprising propionic groups in planar alignment with respect to the molecular structure of said agent.

There are many variations to the assays for screening for antagonists and all are encompassed by the present invention.

When the HA2-containing molecules or derivatives, analogues or homologues thereof are used in a vaccine composition, they may be used as an immunogenic component to stimulate an immune response against the HA2 domain or they may be used as direct antagonists. They may also generate an immune response to other domains since this may cause conformational changes preventing HA2 interaction with a porphyrin-containing molecule such as but not limited to hemoglobin or a precursor form thereof or part thereof such as heme.

Accordingly, another aspect of the present invention provides a composition such as therapeutic or vaccine composition comprising an agent as hereinbefore described and one or more pharmaceutically acceptable carriers and/or diluents.

The immunogenic component of a vaccine composition as contemplated herein exhibits excellent therapeutic activity, for example, in the prophylaxis and/or treatment of *P. gingivalis* infection when administered in an amount which depends on the particular case. For example, for recombinant peptide, polypeptide or protein molecules, from about 0.5 µg to about 20 mg, may be administered, preferably from about 1 µg to about 10 mg, more preferably from about 10 µg to about 5 mg, and most preferably from about 50 µg to about 1 mg equivalent of the immunogenic component in a volume of about 0.01 ml to about 5 ml or from about 0.1 ml to about 5 ml. The important feature is to administer sufficient immunogen to induce a protective immune response. The above amounts can be administered as stated or calculated per kilogram of body weight. Dosage regime can be adjusted to provide the optimum therapeutic response. For example, several divided doses can be administered or the dose can be proportionally reduced as indicated by the exigencies of the therapeutic situation. Booster administration may also be required.

The vaccine of the present invention can further comprise one or more additional immunomodulatory components such as, for example, an adjuvant or cytokine molecule, amongst others, which is capable of increasing the immune response against the immunogenic component. Non-limiting examples of adjuvants that can be used in the vaccine of the present invention include the RIBI adjuvant system (Ribi Inc., Hamilton, Mont., USA), alum, mineral gels such as aluminium hydroxide gel, oil-in-water emulsions, water-in-oil emulsions such as, for example, Block co-polymer (CytRx, Atlanta Ga., USA), QS-21 (Cambridge Biotech Inc., Cambridge Mass., USA), SAF-M (Chiron, Emeryville Calif., USA), AMPHIGEN® adjuvant, Freund's complete adjuvant; Freund's incomplete adjuvant; and Saponin, QuilA or other saponin fraction, monophosphoryl lipid A, and Avridine lipid-amine adjuvant. Other immunomodulatory agents that can be included in the vaccine include, for example, one or more cytokines, such as interferon and/or interleukin, or other known cytokines. Non-ionic surfactants such as, for example, polyoxyethylene oleyl ether and n-hexadecyl polyethylene ether may also be included in the vaccines of the present invention.

The vaccine composition can be administered in any convenient manner such as by oral, intravenous (where water soluble), intramuscular, subcutaneous, intranasal, intradermal or suppository routes or by implantation (e.g. using slow release technology). Depending on the route of administration, the immunogenic component may be required to be coated in a material to protect it from the action of enzymes, acids and other natural conditions which may inactivate it, such as those in the digestive tract.

The vaccine composition may also be administered parenterally or intraperitoneally. Dispersions can also be prepared in glycerol, liquid polyethylene glycols, and mixtures thereof, or in oils. Under ordinary conditions of storage and use, these preparations can contain a preservative to prevent the growth of microorganisms. Alternatively, the vaccine composition can be stored in lyophilized form to be rehydrated with an appropriate vehicle or carrier prior to use.

Pharmaceutical forms suitable for injectable use include sterile aqueous solutions (where water soluble) or dispersions and sterile powders for the extemporaneous preparation of sterile injectable solutions or dispersions. In all cases the form must be fluid to the extent that easy syringeability exists, unless the pharmaceutical form is a solid or semi-solid such as when slow release technology is employed or it may be deliverable by spray, inhalation, nasal drip or microdroplets. In any event, it must be stable under the conditions of manufacture and storage and must be preserved against the contaminating action of microorganisms.

The carrier may be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents such as, for example, parabens, chlorobutanol, phenol, sorbic acid, thimerosal and the like. In many cases, it will be preferable to include isotonic agents such as, for example, sugars or sodium chloride. Prolonged absorption of the injectable compositions can be brought about by the use in the compositions of agents delaying absorption such as, for example, aluminum monostearate and gelatin.

Sterile injectable solutions are prepared by incorporating the active compound in the required amount in the appropriate solvent with various of the other ingredients enumerated above, as required, followed by filter-sterilization. Generally, dispersions are prepared by incorporating the sterilized active ingredient into a sterile vehicle which contains the basic dispersion medium and the required other ingredients selected from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Compositions comprising antagonists are formulated in a manner similar to transformation of an immunogenic composition.

The present invention extends to vaccine compositions which confer protection against infection by one or more isolates or sub-types of *P. gingivalis* including those that belong to the same serovar or serogroup as *P. gingivalis*. The vaccine composition preferably also confers protection against infection by other species of the genus *Prophyromonas* or other microorganisms related thereto as determined at the nucleotide, biochemical, structural, physiological and/or immunointeractive level; the only requirement being that said other species or other microorganism produce a peptide, polypeptide or protein which is immunologically cross-reactive to an HA2-containing molecule of *P. gingivalis*. For example, such related microorganisms may comprise genomic DNA which is at least about 70% similar overall to the genomic DNA of *P. gingivalis* as determined using standard genomic DNA hybridization and analysis techniques.

The terms "serogroup" and "serovar" relate to a classification of microorganisms which is based upon serological typing data, in particular data obtained using agglutination assays such as the microscopic agglutination test (MAT). Those skilled in the art will be aware that serovar and serogroup antigens are a mosaic on the cell surface and, as a consequence there will be no strict delineation between bacteria belonging to a serovar and/or serogroup. Moreover, organisms which belong to different species may be classified into the same serovar or serogroup because they are indistinguishable by antigenic determination. As used herein, the term "serovar" means one or more *P. gingivalis* strains which are antigenically-identical with respect to antigenic determinants produced by one or more loci. Quantitatively, serovars may be differentiated from one another by cross-agglutination absorption techniques. As used herein, the term "serogroup" refers to a group of *Porphyromonas* spp. whose members cross-agglutinate with shared group antigens and do not cross-agglutinate with the members of other groups and, as a consequence, the members of a serogroup have more or less close antigenic relations with one another by simple cross-agglutination.

The present invention extends further to vaccine compositions capable of conferring protection against a "genetic variant" of *P. gingivalis*, the only requirement being that such a variant produce an HA2-containing peptide, polypeptide or protein capable of binding to an HA2-binding motif on a porphyrin-containing molecule. For example, the HA2- containing molecule may comprise at least about 40% similarity with respect to a *P. gingivalis* protein or at least about 20% identity after optimum alignment with same sequence.

The present invention further extends to combination vaccines comprising an effective amount of an immunogenic component of the present invention combined with an effective amount of one or more other antigens or therapeutic molecules capable of protecting the subject against other pathogens or disease conditions.

Particularly useful therapeutic compositions comprise antibodies to the porphyrin-binding motif of the HA2 domain or to other regions of the HA2 domain but which conformationally inhibits porphyrin binding.

The present invention further provides for the use of a gingipain or an HA2 domain containing part thereof or other HA2-containing molecule in the manufacture of a medicament for the prevention or treatment of infection by *P. gingivalis* or related microorganism.

In a related aspect of the present invention, there is provided a use of an antagonist of interaction between a HA2-containing molecule from *P. gingivalis* or related microorganism and a porphyrin-containing molecule such as but not limited to hemoglobin or a precursor form thereof or part thereof such as heme in the manufacture of a medicament for the prophylaxis or treatment of *P. gingivalis* infection.

The present invention is further described by the following non-limiting Examples.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

EXAMPLE 1

RgpA and Kgp Isolation

Polydomain RgpA and Kgp were isolated and characterized as described (18) by Arginine-sepharose affinity chromatography of detergent-extracted *P. gingivalis* (ATCC 33277) cells. Alternatively, polydomain RgpA and Kgp were isolated as previously described (19) by arginine-Sepharose affinity chromatography from cell-free supernatant of a 10 d *P. gingivalis* batch culture.

EXAMPLE 2

Enzyme Activity Assays

The proteinase activities of *P. gingivalis* culture fractions were measured using the substrates N-tertiary-butoxycarbonyl-Ile-Glu-Gly-Arg-7-amido-4-methylcoumarin or N-tertiary-butoxy-carbonyl-Glu-Lys-Lys-7-amido-4-methylcoumarin at 30 C in Tris buffer without added reducing agents. Substrate hydrolysis was monitored over time by absorption at 460 nm using a 380 nm excitation beam on a PERKIN ELMER® LS 50B luminescence spectrophotometer.

EXAMPLE 3

Development of Monoclonal Antibodies 5A1 and IIB2

Anti-gingipain monoclonal antibodies 5A1 and IIB2 were prepared in mice against gingipains as described (19).

EXAMPLE 4

Expression and Purification of rHA2

Forward and reverse primers (AACCTGCAGCGCGCA-GACTTCACGG SEQ ID NO:2 and GGAAGCCAATG-GCGCCAAAAGATCTAGT SEQ ID NO:3) were designed to amplify the HA2 domain from the *P. gingivalis* Arg-gingipain-1 proteinase gene (Accession Number U15282). Restriction sites for Pst1 and Bgll1 were designed into the 5' ends of the primers to facilitate cloning. Digested Pcr Product was Ligated Into the QIAexpressionist type III construct providing a 6x-His tag on the COOH-terminus (Qiagen Corp., USA). Transformation of the ligated construct was performed by electroporation into *E. coli* NM522 cells. *E. coli* cultures were grown at 37° C. to an $OD^{600}$=0.6 then induced with 0.1 mM isopropyl β-D-thiogalactopyranoside (IPTG) for 6 hours. Cells were harvested and resuspended to 5 ml per gram wet weight in buffer A (8 M Urea, 0.1 mM $NaH_2PO_4$, 0.01 mM Tris-HCl, pH 7.9). The cells were stirred for 2 hrs at room temperature taking care to avoid foaming. This cell lysate was subjected to centrifugation at 31,000 g for 30 min at room temperature to pellet the cellular debris then the supernatant was subjected to ultracentifugation at 130,000 g for 2 hrs. The clarified lysate was loaded onto a nickel-nitrilotriacetic acid column (Ni-NTA, Qiagen Corp., USA) pre-equilibrated with buffer A. The Ni-NA column washed with buffer A until baseline was reached. The protein was refolded on this column by running a linear gradient of urea from 8 M to 0 M in 20 mM Tris-HCl, 500 mM NaCl, 10% v/v glycerol, pH 7.9. The protein was then eluted with 50 mM Tris-HCl, 500 mM NaCl, 10% v/v glycerol, 250 mM imidazole, pH 7.9. The eluant was diluted 100 fold in 50 mM sodium acetate buffer, pH 5.5 and applied to a hemoglobin-agarose column pre-equilibrated with the dilution buffer. After loading, the column washed with the same buffer until baseline was reached then the hemoglobin-binding protein was eluted with 50 mM tris-HCl, pH 9. Protein concentrations were determined by Coomassie dye binding using bovine serum albumin as a standard.

EXAMPLE 5

SDS-PAGE and Western Blotting

SDS-PAGE was performed using 12% w/v gels with 4% w/v stackers by the method of Laemmli (39). All samples were diluted with SDS sample buffer before electrophoresis with (reducing) or without 2-mercaptoethanol. Western blots were performed by the method of Towbin (40) and proteins were transferred from the gels to polyvinyldifluoride (PVDF) paper (BioRad Inc., CA, USA) with 300 mA for 1 hr. Blots were blocked with 0.1% w/v bovine serum albumin in 20 mM Tris-HCl with 500 mM NaCl containing 0.1% v/v Tween 20 (TBS/Tween). An alkaline phosphatase (AP) conjugate of a rabbit anti-mouse IgG (Dako Corp., USA) was used as a secondary antibody. Blots were washed with TBS/Tween between antibody applications. Substrate for AP was nitroblue tetrazolium in excess with 5-bromo-4-chloro-3-indoyl phosphate (NBT/BCIP) (BioRad, Calif., USA) and color was developed in 5 mM Tris, pH 9.5.

$NH_2$-terminal amino acid sequencing of resolved SDS-PAGE proteins was performed as previously described (41).

EXAMPLE 6

ELISA

Enzyme-linked immunosorbant assays (ELISA) were performed in polystyrene microtiter wells. Porphyrins and hemoglobin were used to coat the surfaces in 0.1 M NaOH or bicarbonate buffer pH 9 to determine optimal coating concentrations for saturation binding of rHA2. All wells were blocked and washed in PBS (2.7 mM KCl-1.5 mM $KH_2PO_4$-137 mM NaCl-8.1 mM $Na_2HOP_4$) with 10 mM $NaN_3$ and 0.1% Tween 20 (PBS/Tween). Dilutions of rHA2 in 50 mM acetate buffer pH 5.5 containing 137 mM NaCl, 0.1% Tween and 10 mM $NaN_3$ (Acetate/Tween) were incubated overnight before washing in PBS/Tween. Primary murine monoclonal antibody (VA1) was applied in PBS/Tween at a concentration of 0.5 µg/ml for 1 hr at 37 C. Secondary goat anti-mouse antibodies conjugated with AP (Dako Corp.) were applied at a concentration of 1.1 g/ml for 1 hr at 37 C, and then AP activity was monitored at 414 nm by hydrolysis of the substrate 4-nitrophenylphosphate (Boehringer GmbH, Mannheim, Germany) in 5 mM Tris (pH9.5) by using a TITERTEK TWINREADER PLUS® photometer (absorbance maximum of 3.0 ELISA units). Mean apparent dissociation constants $K_d$s) were derived by solid-phase ELISA as previously described (51).

EXAMPLE 7

Ligand Binding Assay

The ligand-binding assay was a variant of the ELISA in which the ligand (i.e. hemoglobin, deuteroporphyrin 1X dihydrochloride, deuteroporphyrin 1X 2,4 bisethylene glycol, deuteroporphyrin 1X disulfonic acid and dipyrroles with varying placement of the propionate chains) that had been used to coat the wells in bicarbonate buffer or 0.1 M NaOH was subsequently allowed to bind to a second ligand-binding protein (i.e. rHA2) in Acetate/Tween or PBS/Tween. The ligand-binding protein was then detected with MAb VA1, followed by a goat anti-mouse AP conjugate, and developed as already described for ELISA. Bovine hemoglobin was used in these experiments. Deuteroporphyrin 1X 2,4 bisethylene glycol, deuteroporphyrin 1X dihydrochloride, deuteroporphyrin 1X disulfonic acid dihydrochloride, and dipyrroles tested were obtained from Porphyrin Products, Utah, USA.

HA2 domain was cloned, expressed and purified as a six-His tag fusion (51). Nucleic acid and $NH_2$-terminal amino acid sequencing verified the identities of the clone and the expression protein respectively, as the HA2 domain of RgpA.

EXAMPLE 8

Competition Assay

The $IC_{50}$s for ligand binding in solution phase competition assays were determined. By using the standard ligand binding assay described herein, rHA2 at a concentration which produced 50% saturation binding to a hemoglobin-coated plate was preincubated for 1 hr in Acetate/Tween with dilutions of the porphyrins and then allowed to bind to hemoglobin-coated plates overnight. Hemoglobin was used as it was considered to represent the dominant form of porphyrin presentation in the pathological environment of chronic periodontitis.

EXAMPLE 9

Peptide Synthesis

Peptides were synthesized by Chiron Mimotopes (Victoria, Australia) with terminal amines and carboxylic acids. Peptide #1 sequence was ALNPDNYLISKDVTG SEQ ID NO:1. Peptide #2 sequence was GEAPAEWTTI-DADGDGQGWL SEQ ID NO:4. Peptide #3 is ALNPD-NYLISKDVTGATKVKY SEQ ID NO:8. The latter amino acid sequence is encoded by the nucleotide sequence set forth in SEQ ID NO:7.

Peptides were synthesized by Chiron Mimotopes (Victoria, Australia) with terminal amines and carboxylic acids. Peptide #1 sequence was ALNPDNYLISKDVTG SEQ ID NO:1. Peptide #2 sequence was GEAPAEWTTI-DADGDGQGWL SEQ ID NO:4. Peptide #3 is ALNPD-NYLISKDVTGATKVKY SEQ ID NO:8. The latter amino acid sequence is encoded by the nucleotide sequence set forth in SEQ ID NO:7.

EXAMPLE 10

Materials

All chemicals and compounds were purchased from Sigma Corp., NSW, Australia unless otherwise herein specified.

EXAMPLE 11

Statistics

Statistical differences of measurements between the gingipains and rHA2 were determined with one-tailed Student's t-tests.

EXAMPLE 12

Characteristics of RgpA and Kgp

The polydomain Lys-and Arg-gingipains (RgpA and Kgp, respectively) isolated from the CHAPS-extracted *P. gingivalis* cells possessed SDS-PAGE profiles, $NH_2$-terminal sequences, proteolytic activities and inhibition profiles characteristic of gingipain-like molecules previously described (19,34).

The HA2 domain was cloned, expressed, and purified as a 6x His-tag fusion. Nucleic acid and $NH_2$-terminal amino acid sequencing verified the identity of the clone and the expressed protein, respectively, as the HA2 domain of RgpA.

EXAMPLE 13

Hemoglobin is Bound by rHA2 and by Native but not Denatured RgpA and Kgp

Figure 2A:
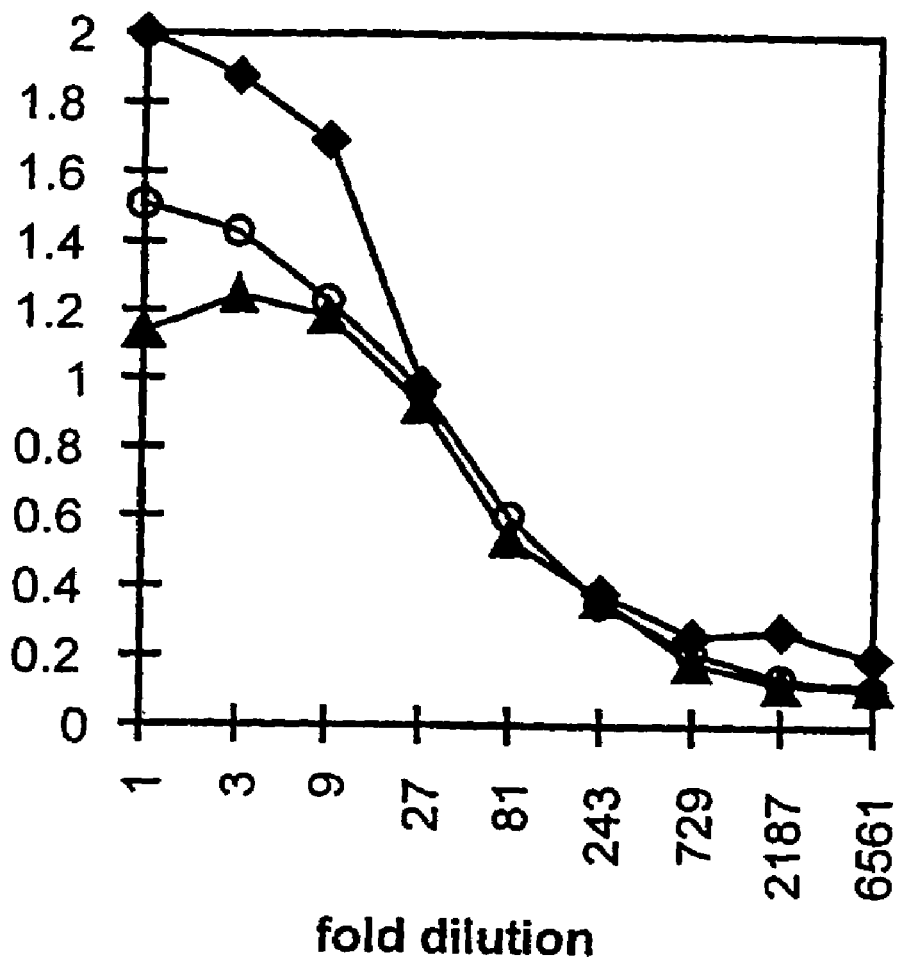
FIGS. 2a and 2b are graphical representations showing hemoglobin binding by rHA2, RgpA, and Kgp. (2a): Microtiter wells were coated with hemoglobin then incubated with 3 fold dilutions of purified rHA2, 2.5 µg/ml (diamonds), RgpA, 5 µg/ml (circles), or Kgp, 5 µg/ml (triangles). Association of rHA2 with hemoglobin was measured with mAb 5A1 followed by substrate development at 414 nm after binding of secondary anti-mouse alkaline phosphatase-conjugated antibody. (2b): Hemoglobin binding by native but not denatured gingipains. Wells were coated with hemoglobin then incubated overnight with dilutions of either Rgp-A (closed circles), Kgp (closed triangles), or RgpA denatured by boiling (open circles) or Kgp denatured by boiling (open triangles). For this experiment, native or denatured gingipains that bound to hemoglobin were recognized with mAb IIB2, which specifically detects both native and denatured gingipains. Primary antibody IIB2 was followed by substrate development at 414 nm after binding of secondary anti-mouse AP-conjugated antibody. Data are representative of three separate experiments.
Figure 2B:
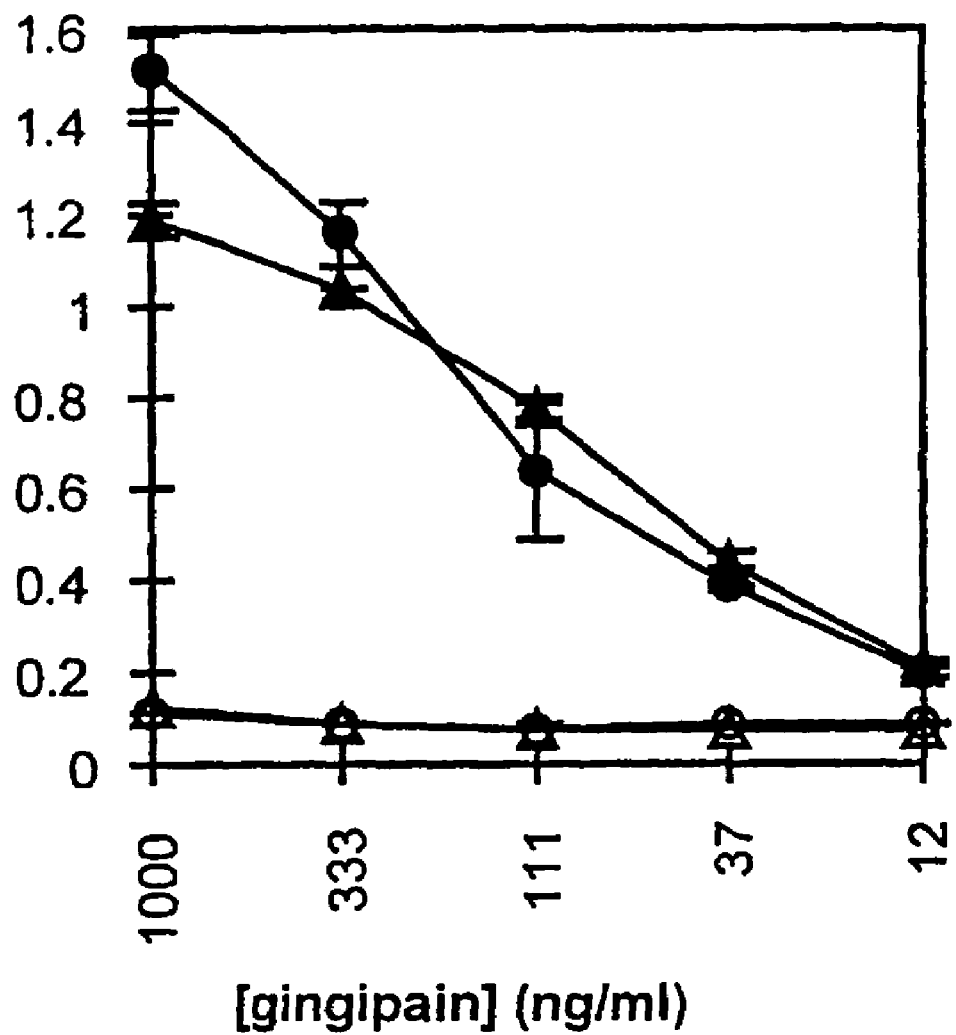

Using the solid-phase ligand binding assay, rHA2, RgpA, and Kgp each bound to hemoglobin (FIG. 2a). As mAb 5A1 was used to detect rHA2 bound to hemoglobin and did not interfere with this binding, it was evident that the epitope for mAb 5A1 within the HA2 domain was separate from the hemoglobin-binding site of HA2. Hemoglobin binding affinities were similar (P=0.24) for the rHA2, RgpA and Kgp ($K_d$=2.1±0.6 nM) and the binding curves of neither the rHA2 nor the gingipains were indicative of multi-site binding (FIG. 2a). High-affinity binding to hemoglobin at a single site within only the HA2 domain of both native RGPA and Kgp is sufficient to account for these observations. The binding site for hemoglobin within the gingipains appeared to be associated with higher-order protein structure since denaturation of RgpA and Kgp by boiling effectively eliminated their ability to bind hemoglobin (FIG. 2b).

EXAMPLE 14

Hemoglobin Binding of the HA2 Domain is Mediated Through the Heme Moiety

Figure 3A:
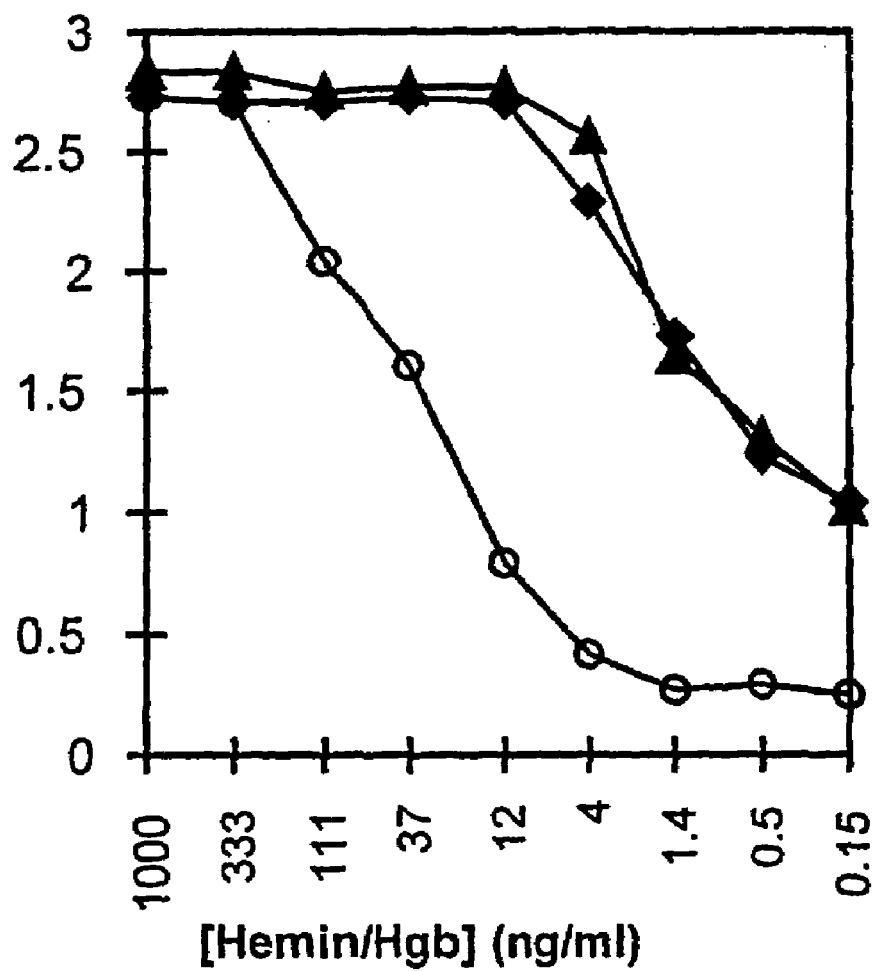
FIGS. 3a and 3b are graphical representations showing binding of the HA2 domain to the heme moiety. (3a): Binding of rHA2 to dilutions of hemin (diamonds), hemoglobin (circles), or hemoglobin degraded by proteinase-K (triangles). Microtiter wells were coated with dilutions of samples then overnight binding of rHA2 to coated wells was detected with mAb 5A1 followed by substrate development at 414 nm after binding of secondary anti-mouse AP-conjugated antibody. The absence of contaminating protein within 90 µg of the hemin preparation and the absence of non-degraded subunits of hemoglobin remaining after proteinase-K treatment was verified by SDS-PAGE (data not shown). (3b): Binding of rHA2 to hemin. Microtiter wells were coated with hemin and overnight binding of rHA2 dilutions was detected with mAb 5A1 as above. Data are representative of two separate experiments.
Figure 3B:
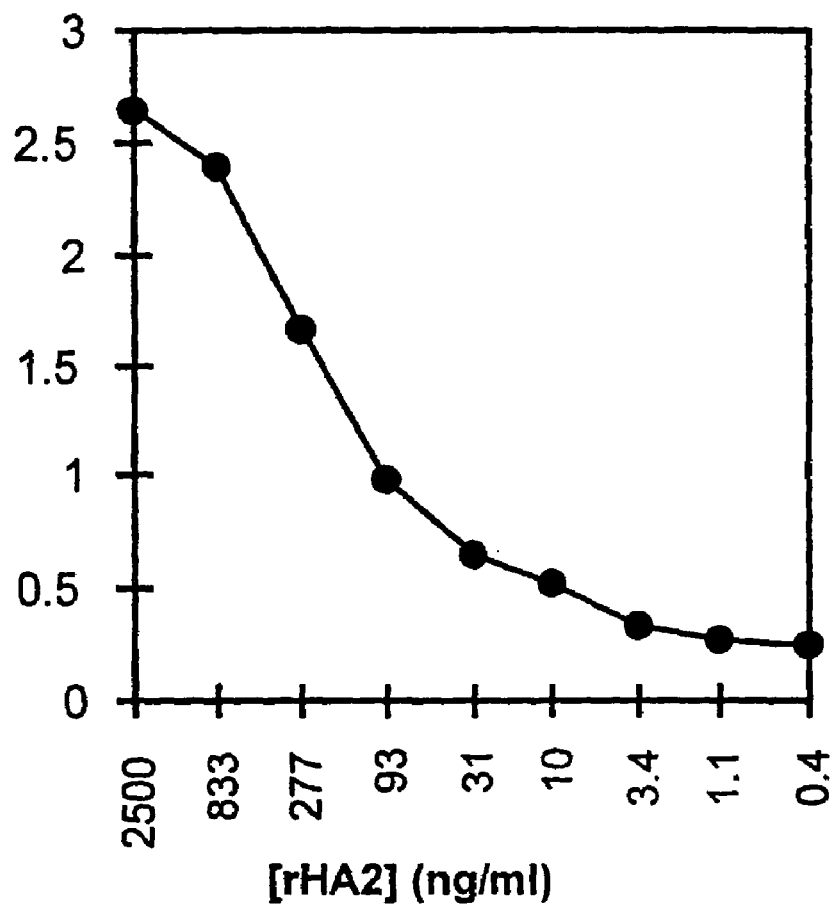

To begin characterizing the binding between rHA2 and hemoglobin, the inventors examined the binding between rHA2 and hemin as well as binding to hemoglobin degraded by proteinase-K. The rHA2 bound not only to wells coated with hemoglobin but also to wells coated with hemin or with the proteolytically degraded hemoglobin (FIG. 3a). Binding of the rHA2 domain to hemin-coated wells was approximately 8 fold weaker than binding to hemoglobin in solid-phase assays ($K_d$=1.6±0.1×10$^{-8}$ M) (FIG. 3b).

EXAMPLE 15

HA2 Domain Binds the Porphyrin Ring Structure

Figure 4A:
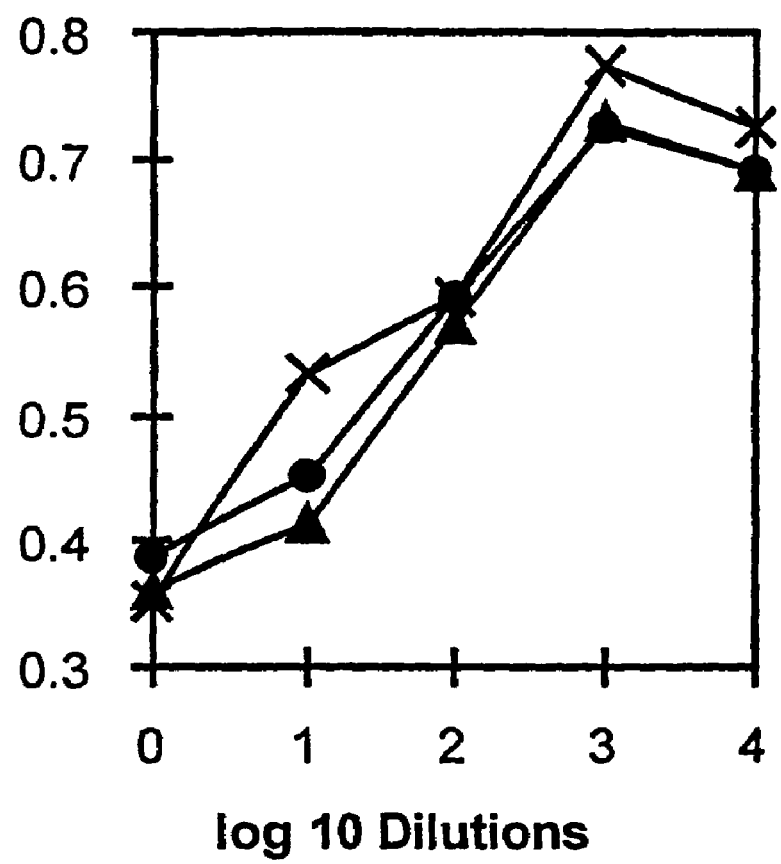
FIGS. 4a and 4b are graphical representations showing inhibition of hemin- or hemoglobin-binding. Microtiter wells were coated overnight with hemin (panel a) or hemoglobin (panel b). rHA2 in *E. coli* lysate (100 fold dilution) (X), 65 ng/ml RgpA (circles) or 65 ng/ml Kgp (triangles) were preincubated with dilutions of 300 µM protoporphyrin IX for 1 hr then transferred to the ligand-coated plates for overnight incubation. Binding of rHA2 or the gingipains to coated wells was detected with mAb 5A1 or mAb IIB2, respectively, followed by substrate development at 414 nm after binding of secondary anti-mouse AP-conjugated antibody. Data are representative of two separate experiments. The absence of contaminating protein in a 90 µg protoporphyrin IX preparation was verified by SDS-PAGE and by Coomassie dye binding.
Figure 4B:
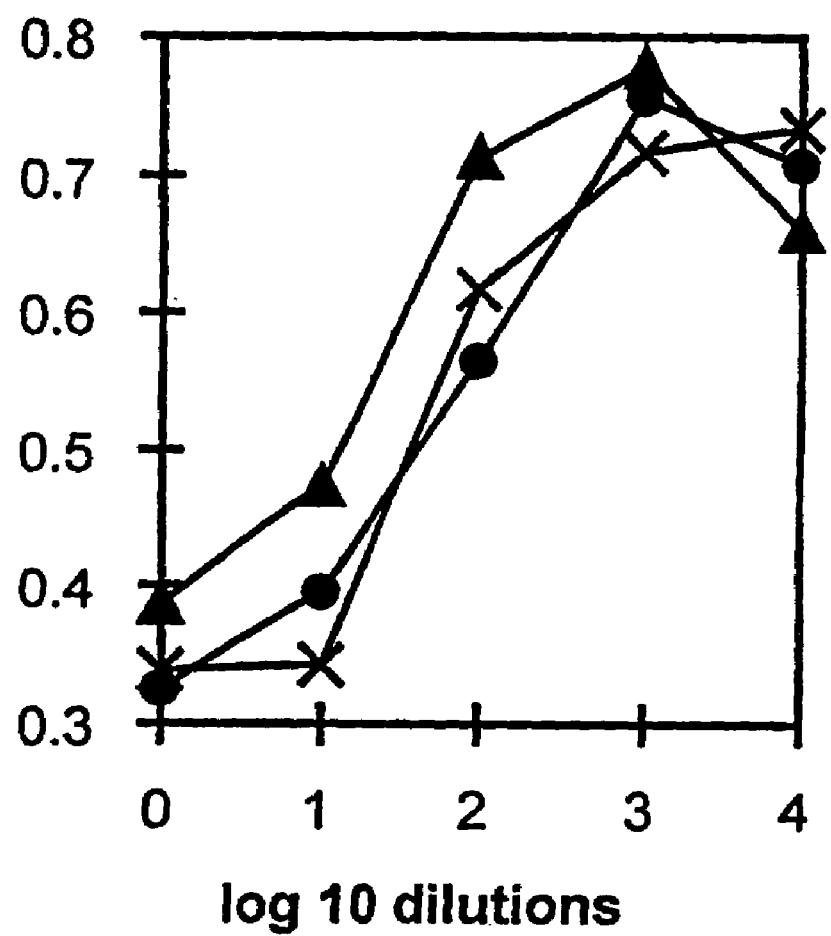
Figure 5A:
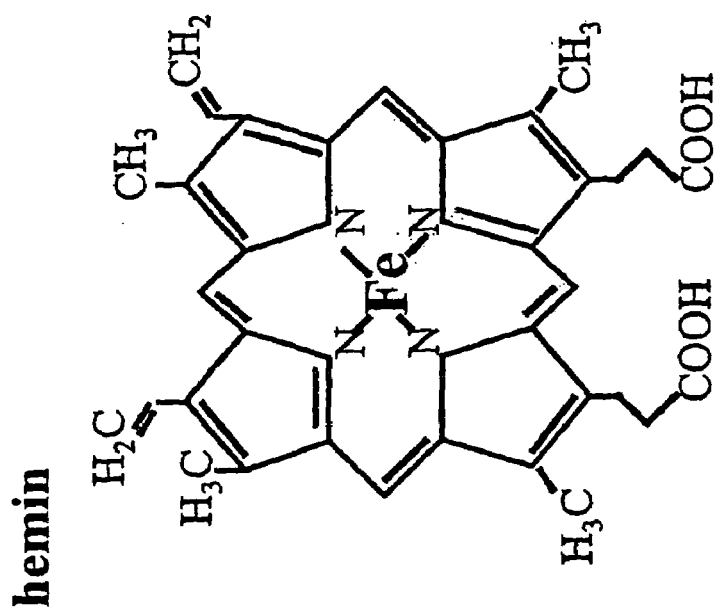
FIGS. 5a, 5b and 5c are diagrammatic representations showing directed porphyrin-binding by rHA2. Microtiter wells were coated with 100 mM ethylene diamine (pH 4.7) then incubated with 90 µg/ml hemin, protoporphyrin IX, or hematoporphyrin overnight in 50% dimethyl formamide in the presence (+) or absence (−) of 10 mM carbodiimide. Wells were washed 4 times with water then the amount of porphyrin bound to the wells was determined by absorbance at 414 nm (striped bars). Wells were blocked with PBS/Tween then incubated with 125 ng/ml rHA2 overnight. Binding of rHA2 to coated wells was detected with mAb 5A1 followed by substrate development at 414 nm after binding of secondary anti-mouse AP-conjugated antibody (solid bars). Error bars represent standard deviation of absorbance measurements. Diagrams of chemical structures for hemin, protoporphyrin IX, and hematoporphyrin are presented adjacent to corresponding data.
Figure 5A:
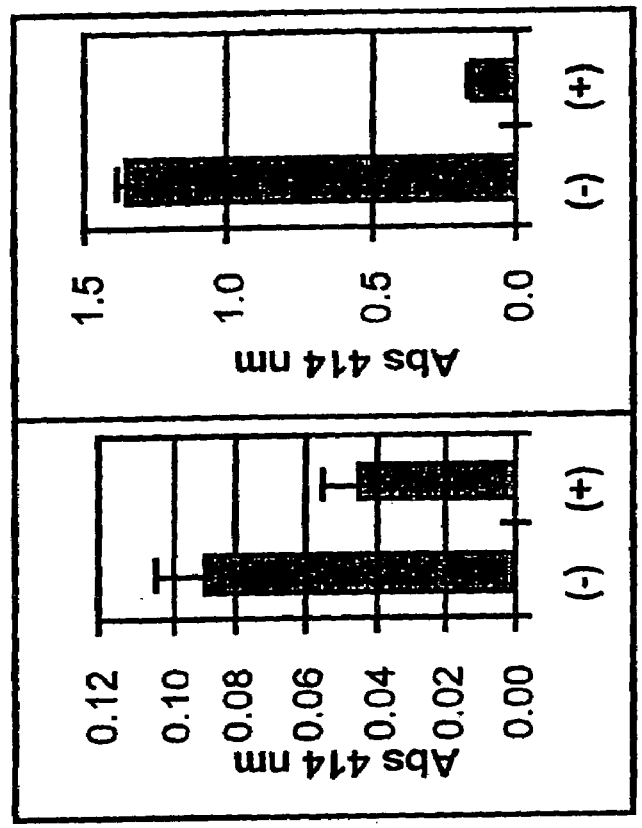
Figure 5B:
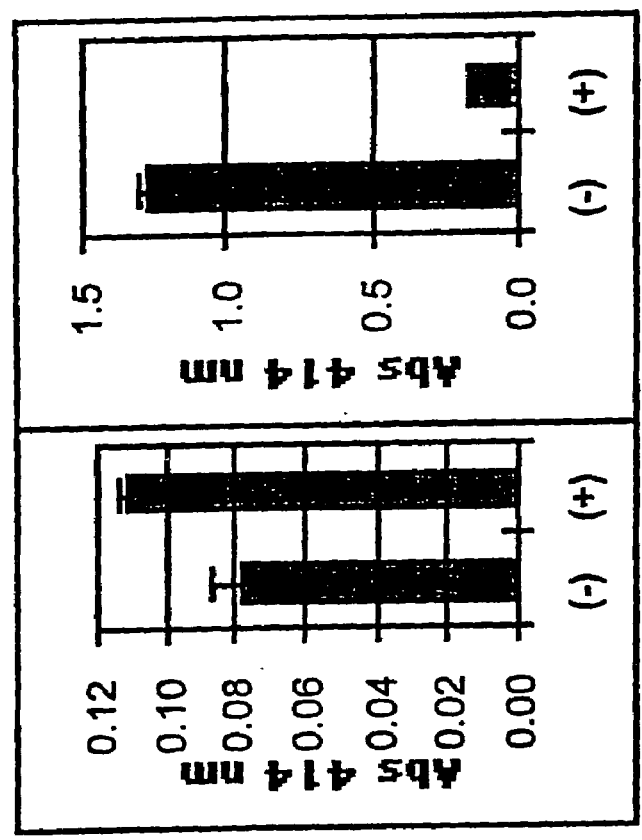
Figure 5B:
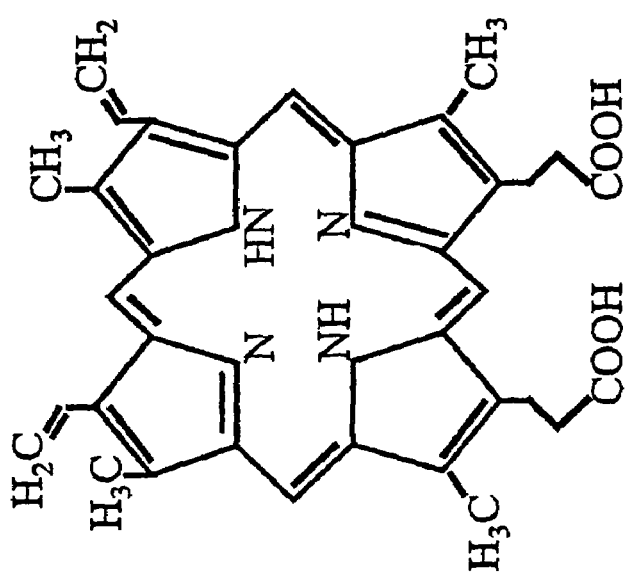
Figure 5C:
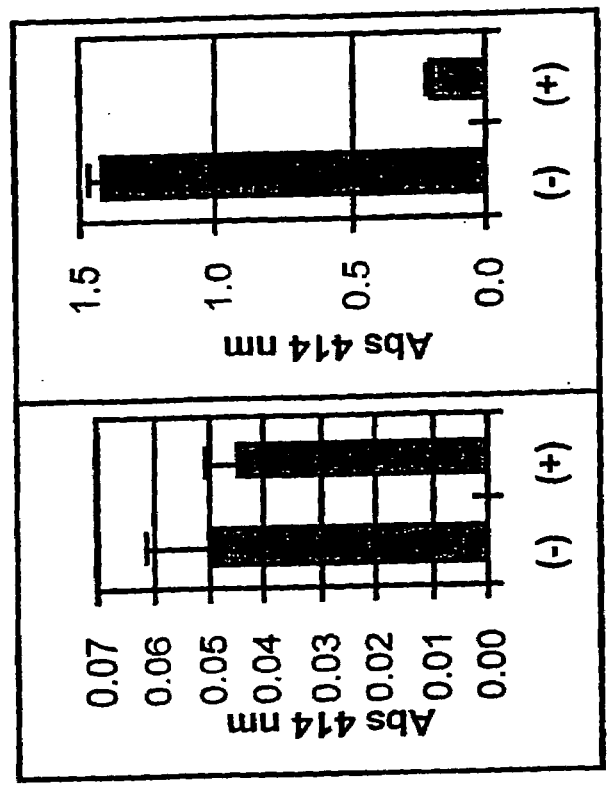
Figure 5C:
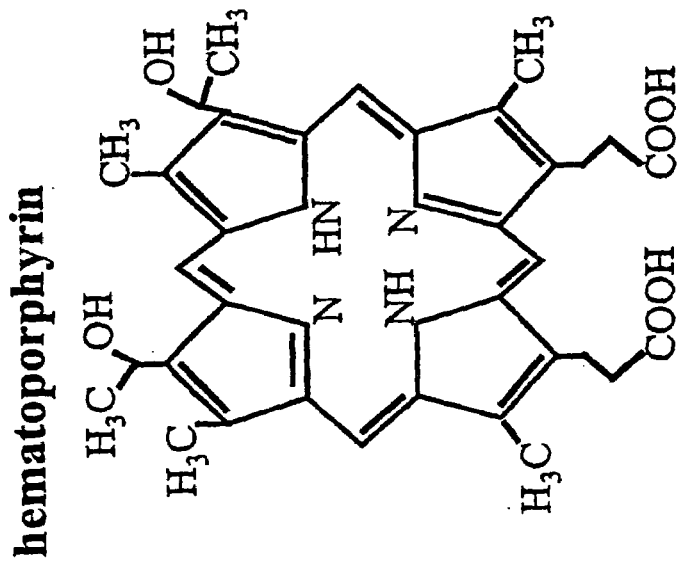

To dissect the binding of the rHA2 domain to hemin, inhibition constants ($IC_{50}$) of the iron-free protoporphyrin IX in solution-phase competition assays were determined. Using the standard ligand binding assay described herein, rHA2 or the gingipains were preincubated with dilutions of protoporphyrin IX then allowed to bind to the hemin-coated wells. Binding of the gingipains or rHA2 to hemin was inhibited with the addition of protoporphyrin IX ($IC_{50}$≈2.5±0.3 µM) (FIG. 4a). $IC_{50}$ values were similar between rHA2 and gingipains (P=0.42). These data indicated that binding of rHA2 or the gingipains to hemin was specific for some aspect of the protoporphyrin ring. Importantly, binding of rHA2 or the gingipains to hemoglobin was also inhibited with protoporphyrin IX (FIG. 4b) ($IC_{50}$=10±2 µM) and pre-incubation with the protoporphyrin could effectively eliminate binding to hemoglobin.

EXAMPLE 16

Directed Protoporphyrin Binding by Recombinant HA2 (rHA2)

Examination of the hemoglobin crystal structure indicated that only the region of the heme moiety possessing the propionate functional groups (FIG. 5) would be exposed for possible protein/protein contact. The inventors reasoned, therefore, that blocking access to the acidic region of protoporphyrin molecules would have an effect on rHA2-binding and allow more specific characterization of binding between the HA2 domain and the porphyrin ring. Modifying the ligand binding assay system used above, surfaces were first coated with ethylene diamine to provide fixed, free, primary amines for carbodiimide linkage of carboxylic acid groups. Hemin, protoporphyrin IX, and hematoporphyrin bound to wells coated with ethylene diamine with or without carbodiimide treatment as determined by absorbance at 414 nm (FIG. 5, striped bars). rHA2-binding to the carbodiimide-treated porphyrins in the wells was almost eliminated, however, compared to the relatively greater association of the rHA2 with the non-derivatized porphyrins (FIG. 5, solid bars). These data indicated that the rHA2 domain specifically recognized the three porphyrin compounds in the region of the propionic acid groups, as we were able to block rHA2-binding by directionally attaching the carboxylic acids of hemin, protoporphyrin IX, or hematoporphyrin to fixed amines. Since the heme moiety within hemoglobin is almost identical to these porphyrin molecules, the data suggested that the heme moiety of hemoglobin was bound by rHA2 and by the HA2 domain of the gingipains in a similar, directed, high-affinity manner.

EXAMPLE 17

Figure 6A:
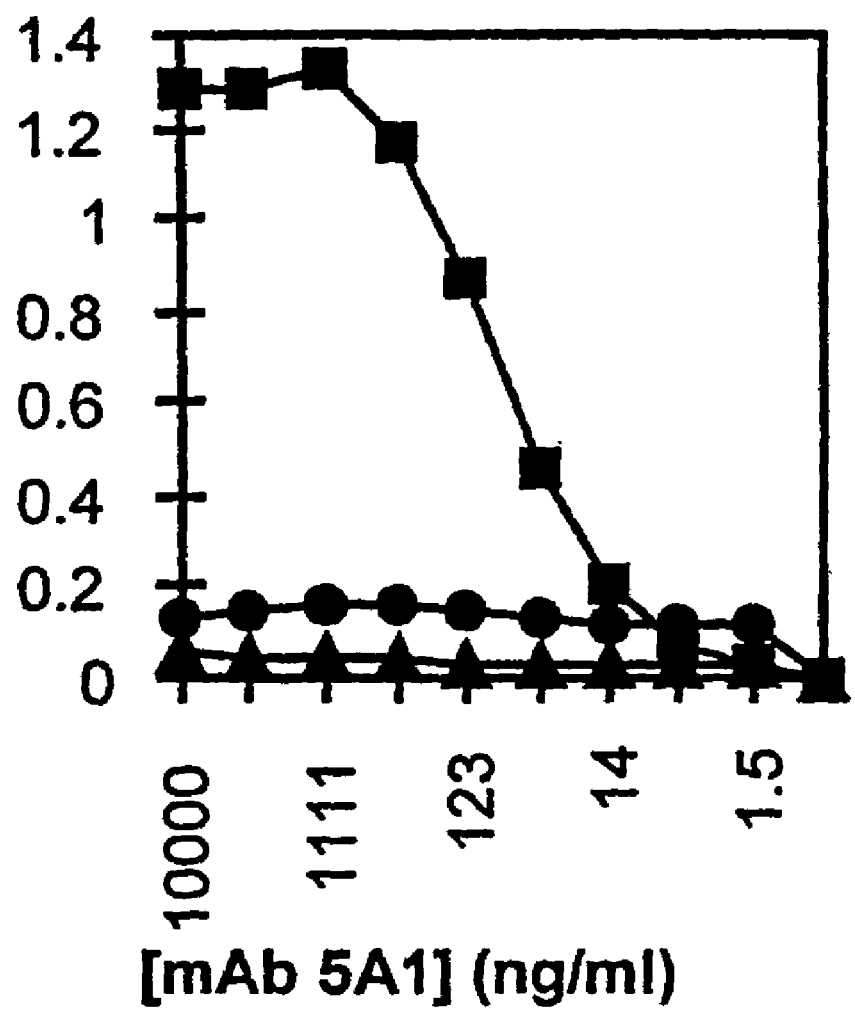
FIGS. 6a, 6b and 6c are graphical representations showing measurement of high-affinity binding of mAb 5A1 with rHA2 gingipains and gingipains from the culture supernatant. (6a): RgpA (circles), Kgp (triangles) or rHA2 in crude *E. coli* lysate (squares) were coated onto microtiter wells and incubated with serial dilutions of mAb 5A1. (6b): Dilutions of Rgp-A (open circles), Kgp (open triangles), or heat denatured Rgp-A (closed circles) or Kgp (closed triangles) were coated onto microtiter wells with 3 fold dilutions from 10 µg/ml then incubated with mAb 5A1. (6c): Purified rHA2 (squares) or purified high molecular-weight aggregates of gingipain domains isolated from culture supernatant (circles) were coated onto microtiter wells and incubated with serial dilutions of mAb 5A1. Data are representative of three separate experiments.
Figure 6B:
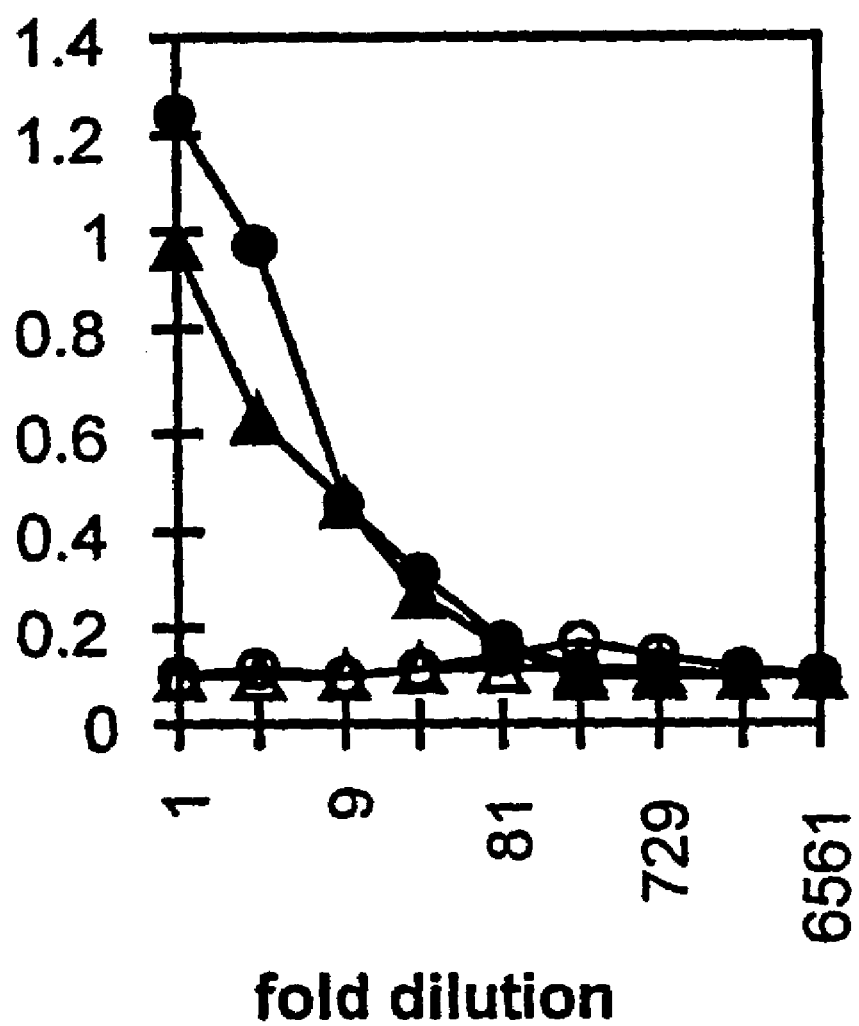
Figure 6C:
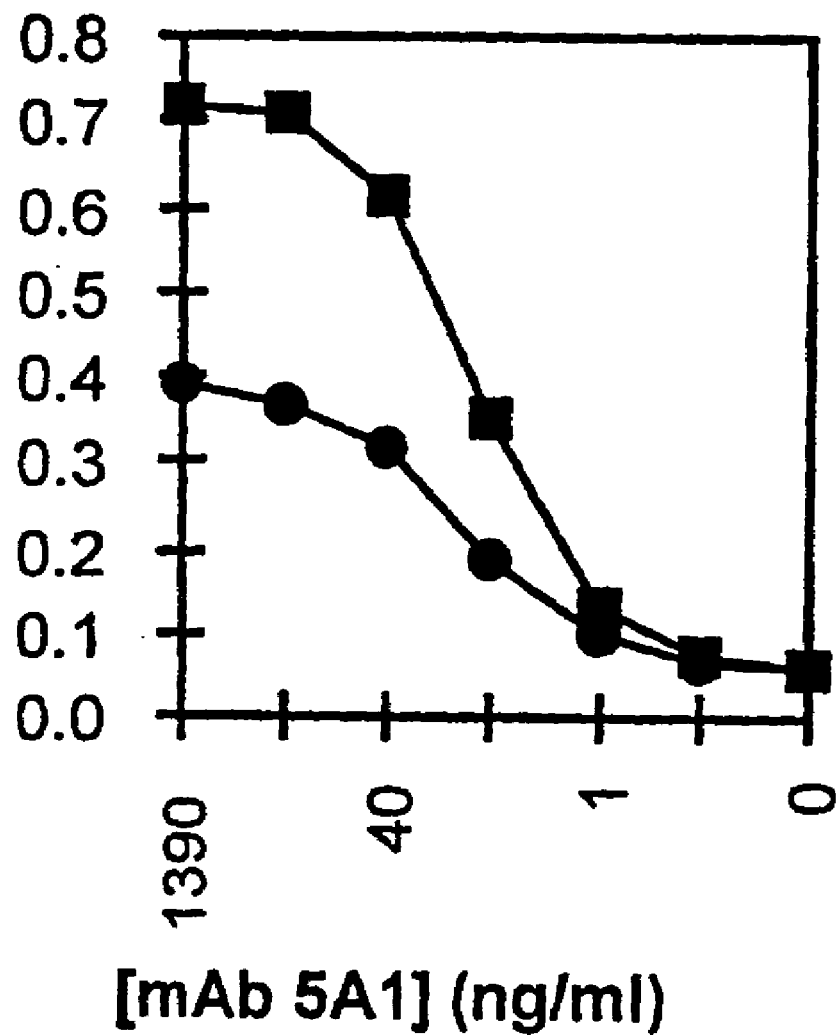

Epitope of mAb 5A1 is Recognized in Recombinant HA2 Domain and in RgpA and Kgp In ELISA, mAb 5A1 bound to the rHA2 with a high affinity ($K_d$=2.2±0.5×10$^{-10}$ M) (FIG. 6a). mAb 5A1 also bound to RgpA and Kgp isolated from the CHAPS-extracted P. gingivalis cells (FIG. 6b). Soluble high molecular-weight aggregates of gingipain domains isolated from the cell-free fraction of a P. gingivalis batch culture by arginine-Sepharose affinity chromatography[34] were, however, recognized by mAb 5A1 ($K_d$=1.7±0.6×10$^{-10}$ M) (FIG. 6c). Similarity of dissociation constants (P=0.36) and of the binding curves suggested that mAb 5A1 recognized the same HA2 epitope in these polydomain gingipains as in rHA2.

EXAMPLE 18

Figure 7:
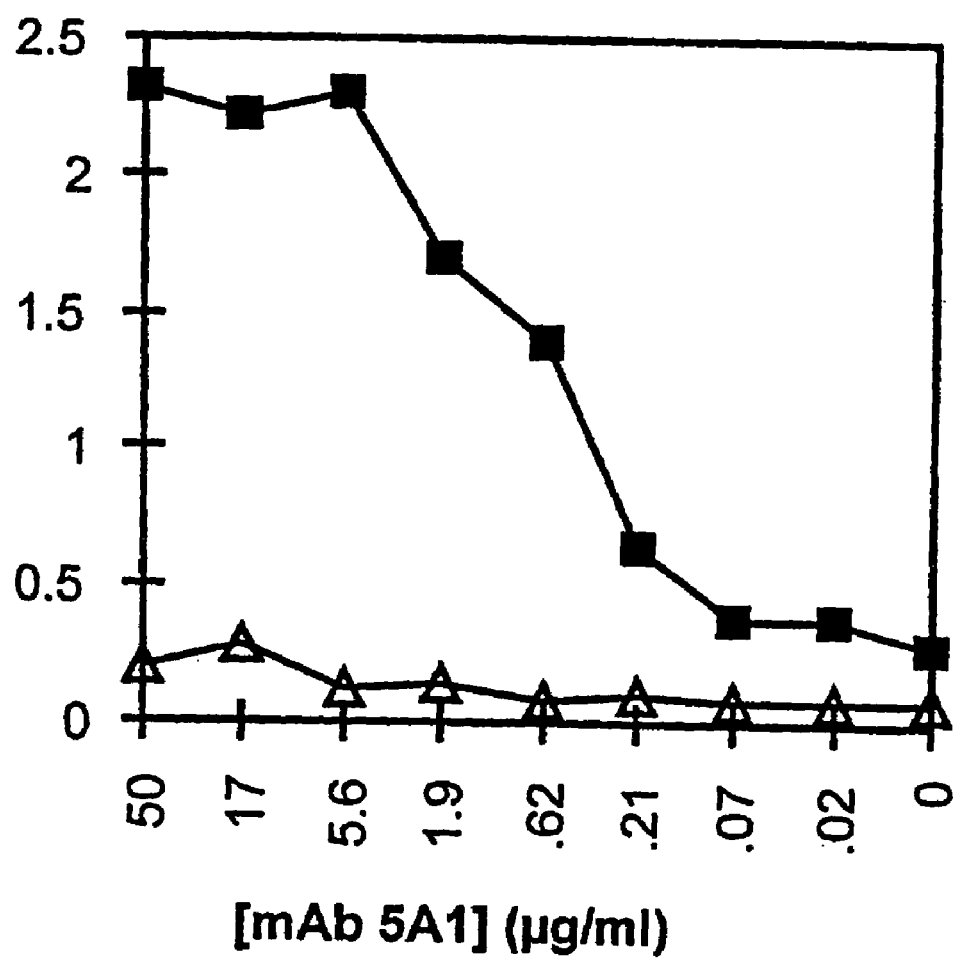
FIG. 7 is a graphical representation showing immunoreactivity of synthetic peptides with mAb 5A1. ELISA demonstrating selective immunoreactivity of mAb 5A1 with peptide #1. Peptide #1 (squares) or peptide #2 (triangles) were coated onto microtiter plates at a concentration of 5 µg/ml overnight then incubated with dilutions of mAb 5A1. Data are representative of two separate experiments.

Epitope of mAb 5A1 is Represented by an Amino Acid Sequence within the HA2 Gingipain Domain Using linear synthetic peptides, the epitope of mAb 5A1 was determined to be associated with the peptide ALNPD-NYLISKDVTG SEQ ID NO:1 ($K_d$=3.8 nM) which represents amino acids #1215-1229 of the translated Kgp within the HA2 domain (FIG. 7, peptide #1). Dot blot analysis on PVDF membrane confirmed the unique immunoreactivity of this peptide with mAb 5A1. Similar results were obtained with peptide #3 SEQ ID NO:8. A search of SwissProt database for the linear sequence of peptide #1 or GEN-BANK® database using the deduced nucleic acid sequence of this epitope resulted in no molecules with perfect homology to the peptide other than the gingipains and HagA, a large hemagglutinin with regions of identity to the entire HA2 domain.

EXAMPLE 19

Figure 8A:
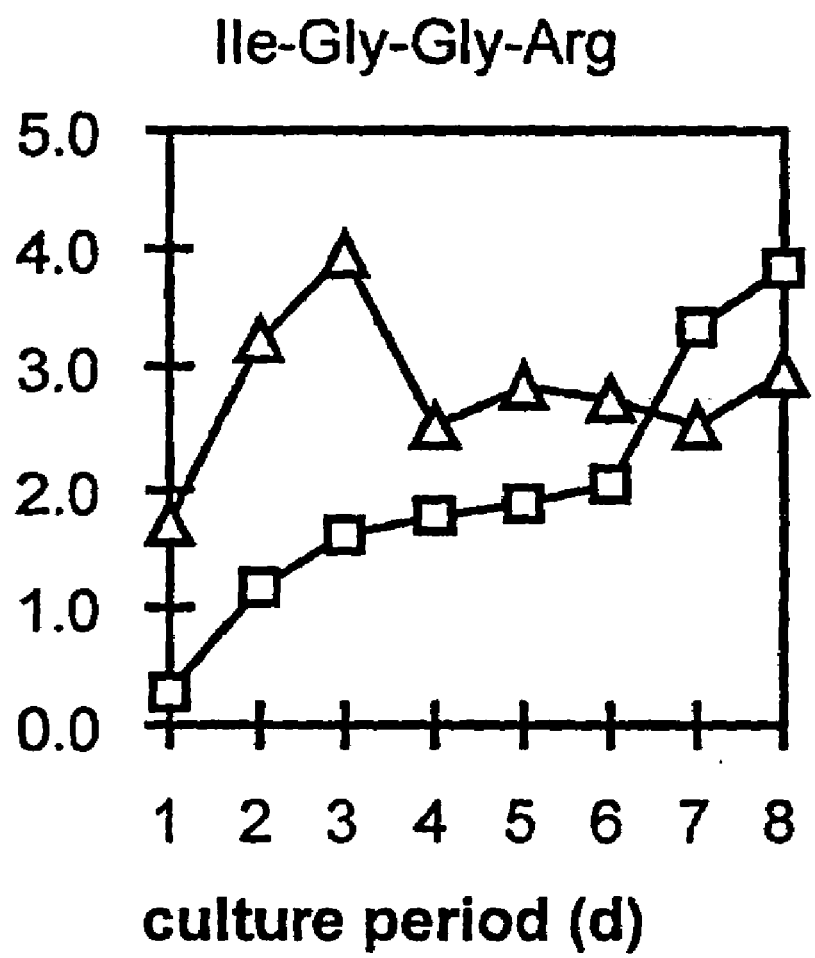
Figure 8B:
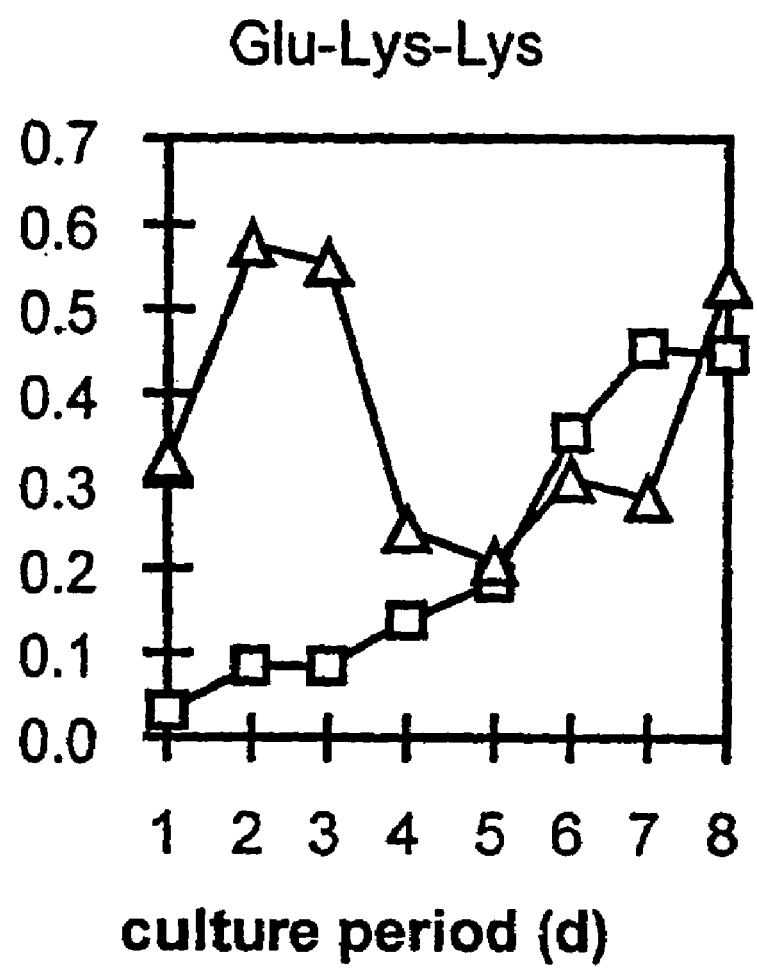

Correlation of HA2 Domain Immunoreactivity with Hemoglobin Binding in P. gingivalis Culture Detection of the HA2 epitope with mAb 5A1 in unfractionated P. gingivalis samples was correlated with hemoglobin binding. Because proteinase activity and gingipain expression have been shown to progressively change during the course of an extended *P. gingivalis* batch culture (34), the inventors examined cell-associated and extra-cellular fractions during 8 days of culture. Both Arg- and Lys-specific proteinase activities of the *P. gingivalis* cells peaked near the third day of culture (FIGS. 8a and b, triangles). Proteinase activities of the cell-free culture supernatants steadily rose throughout the culture period (FIGS. 8a and b, squares).

Figure 8C:
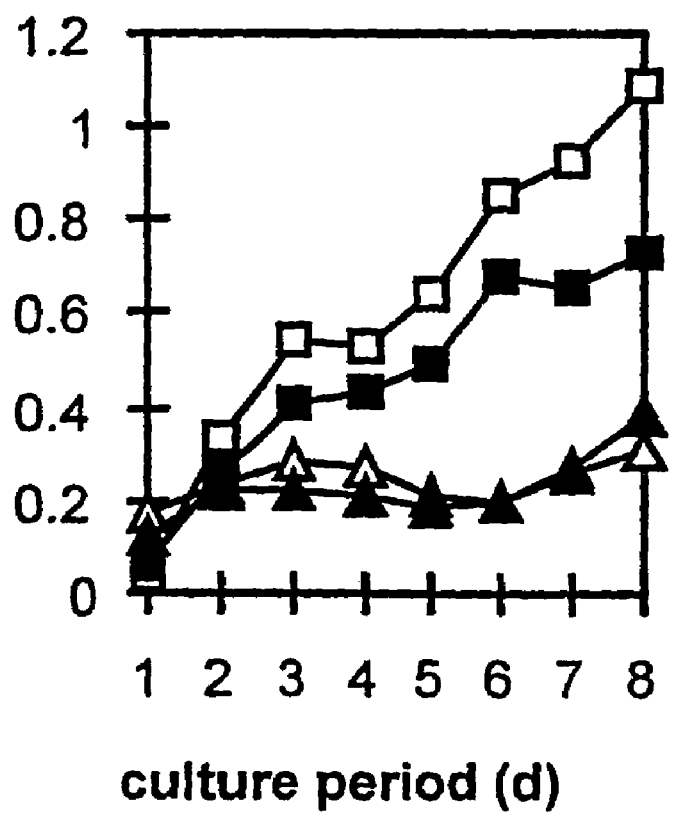
Figure 9A:
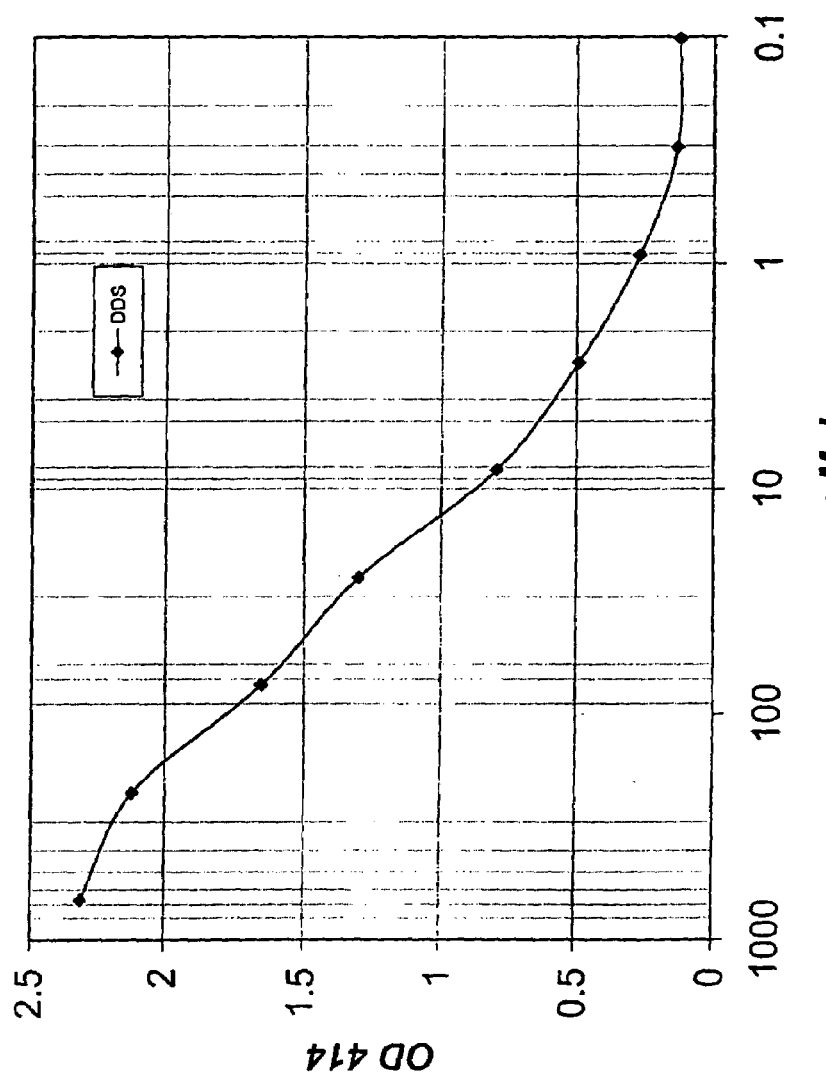
FIGS. 9a, 9b, 9c, 9d and 9e are graphical representations of ligand binding to decreasing concentrations of rHA2. The ligands employed were: (a) deuteroporphyrin 1X 2,4 disulfonic acid (DDS); (b) deuteroporphyrin 1X 2,4 bisethylene glycol (DBEG); (c) dipyrrole 1 (C1; see FIG. 10); (d) dipyrrole 2 (C2; see FIG. 10); (e) dipyrrole 3 (C3; see FIG. 10). Binding between the ligand and rHA2 was detected with monoclonal antibody (MAb) VAI followed by goat anti-mouse AP conjugate.
Figure 9B:
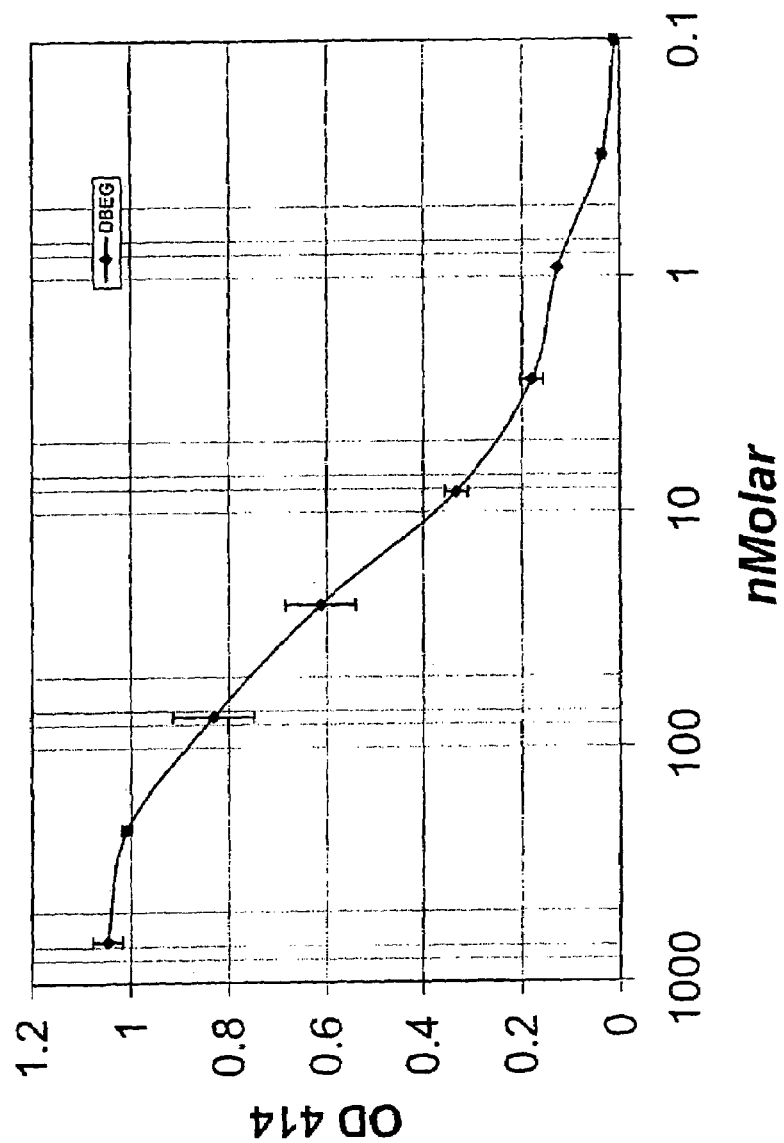
Figure 9C:
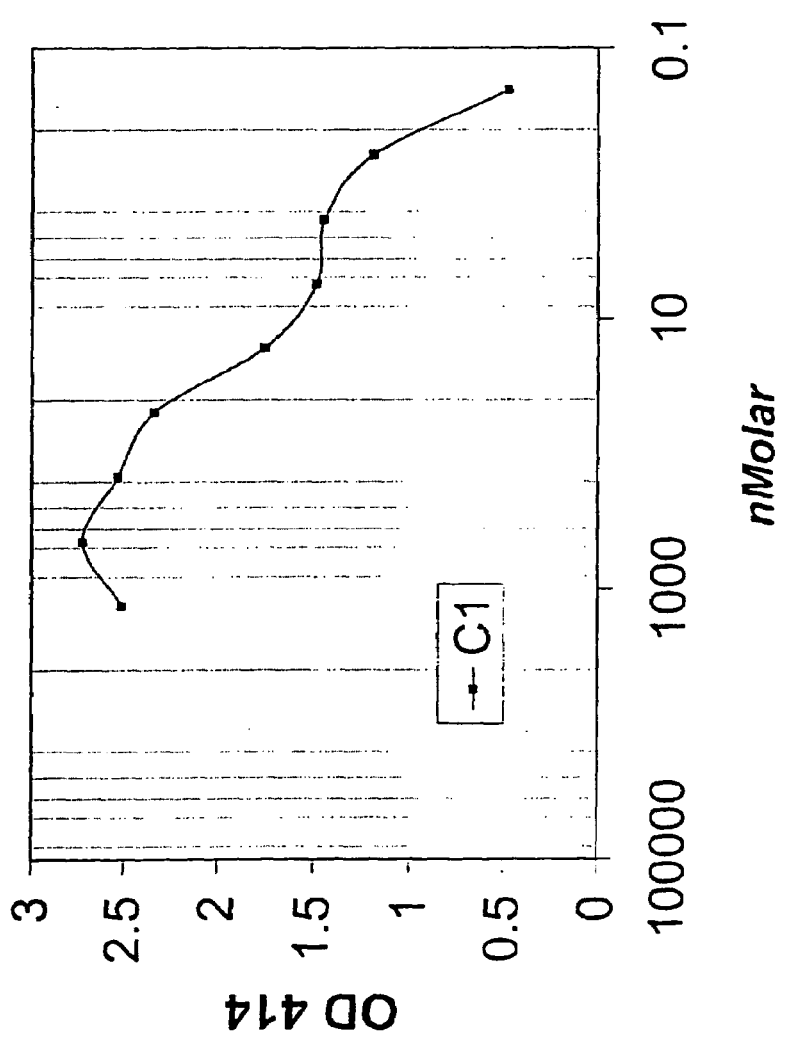
Figure 9D:
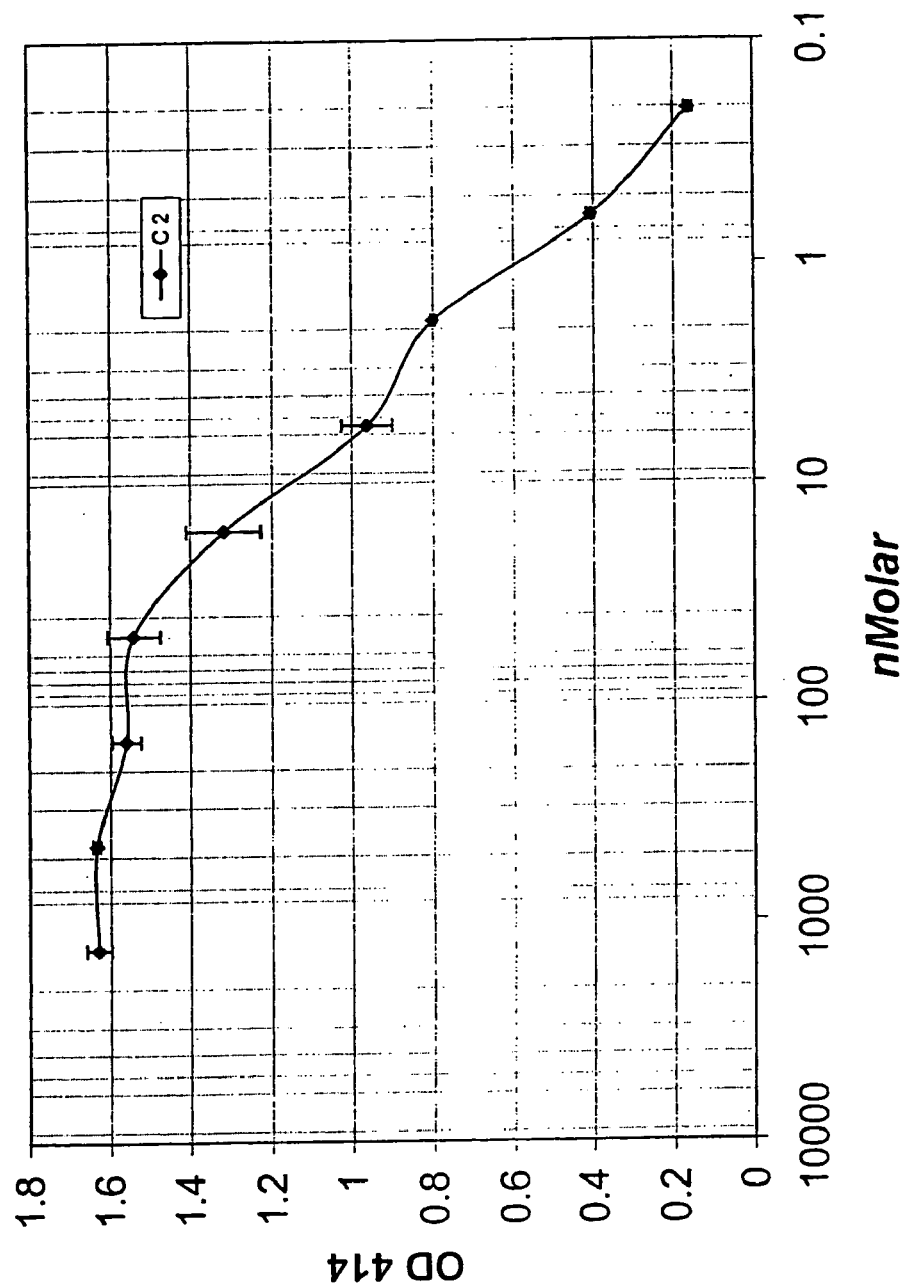
Figure 9E:
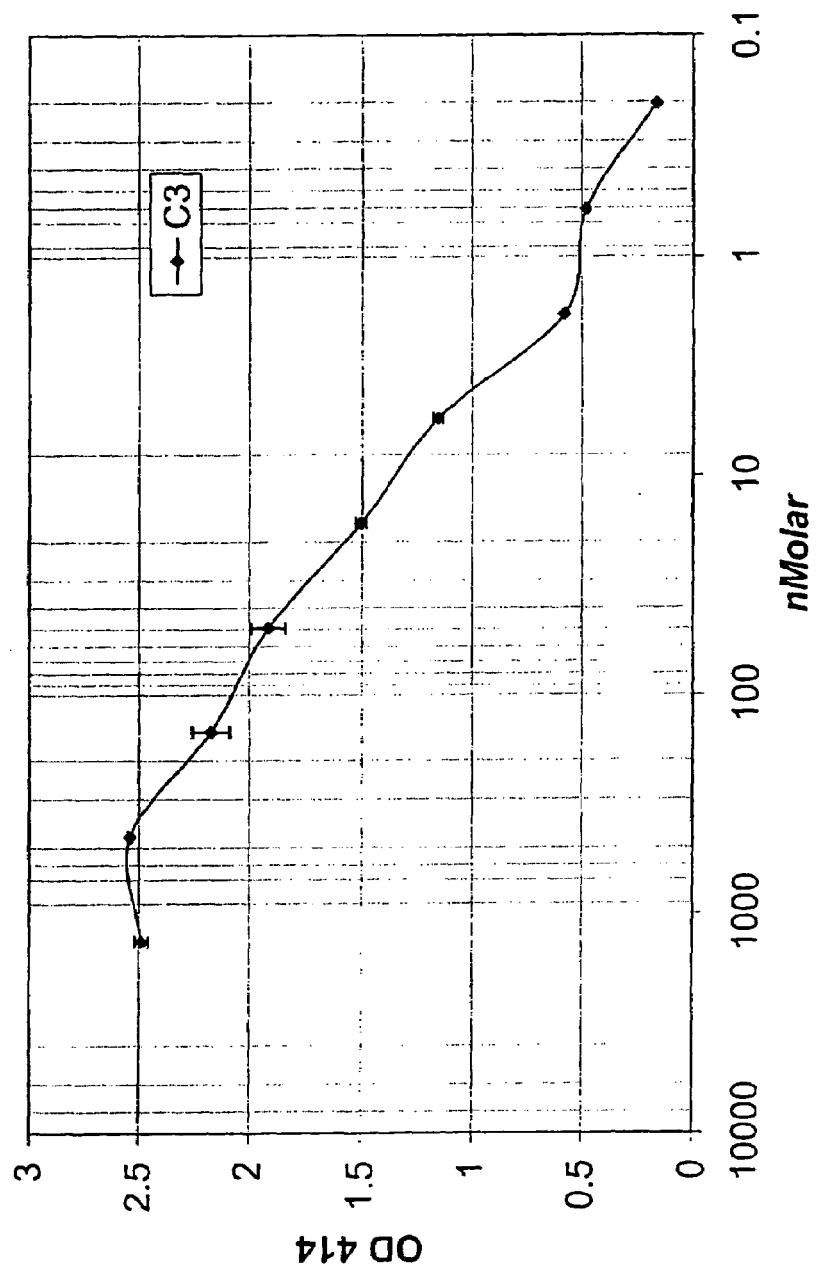
Figure 10A:
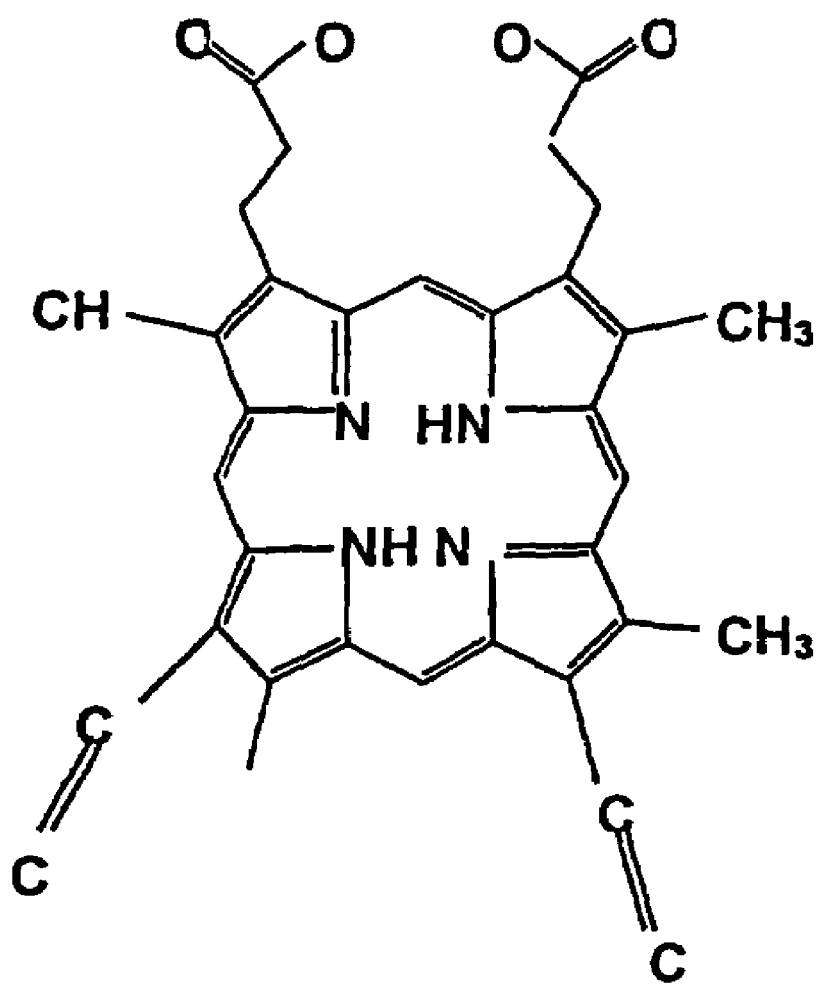
FIGS. 10a, 10b, 10c, 10d, 10e, 10f and 10g are diagrammatic representations of dipyroles 1 (C1), 2 (C2) and 3 (C3) and the porphyrins protoporphyrin 1X (PPIX), deuteroporphyrin 1X 2,4 dihydrochloride (DDH), deuteroporphyrin 1X 2,4 disolfonic acid (DDS) and deuteroporphyrin 1X 2,4 bisethylene glycol (DBEG).
Figure 10B:
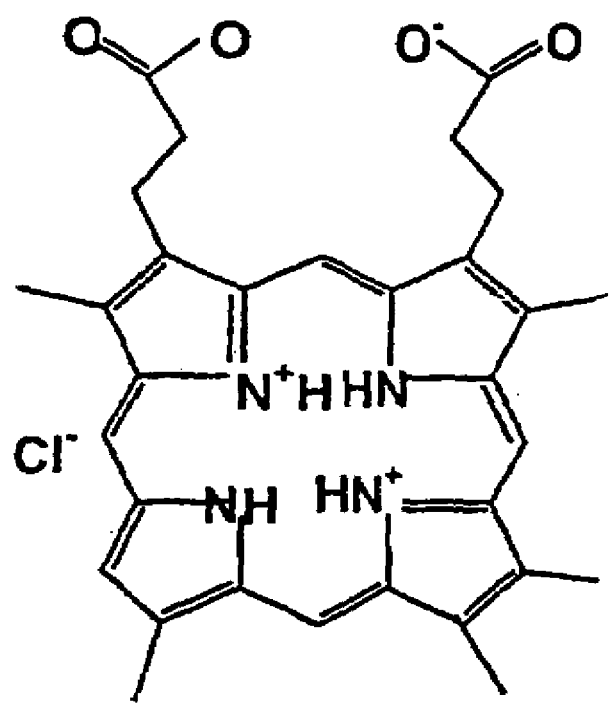
Figure 10C:
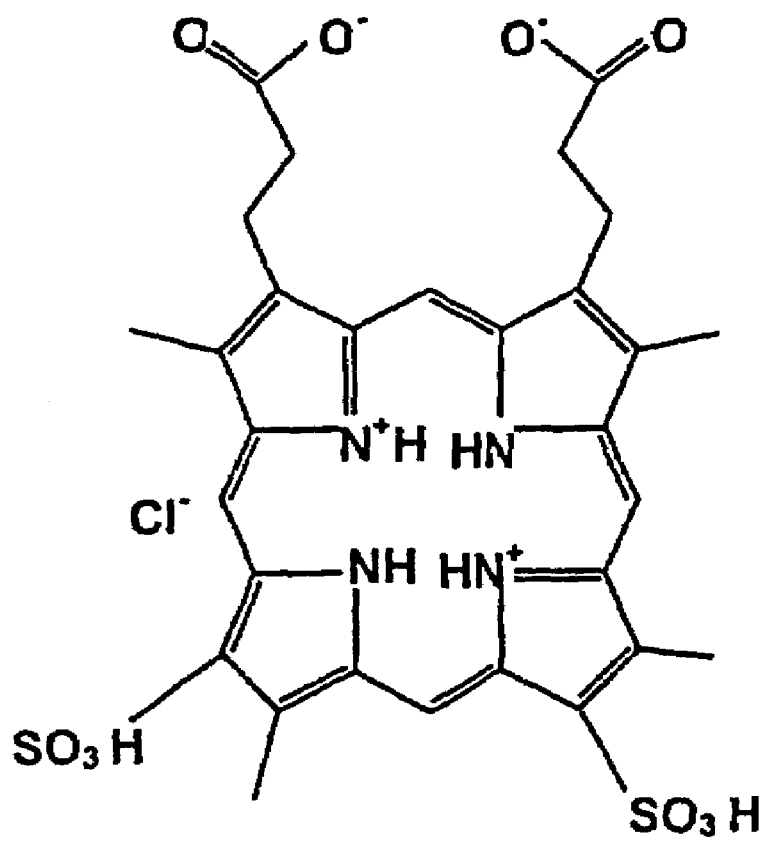
Figure 10D:
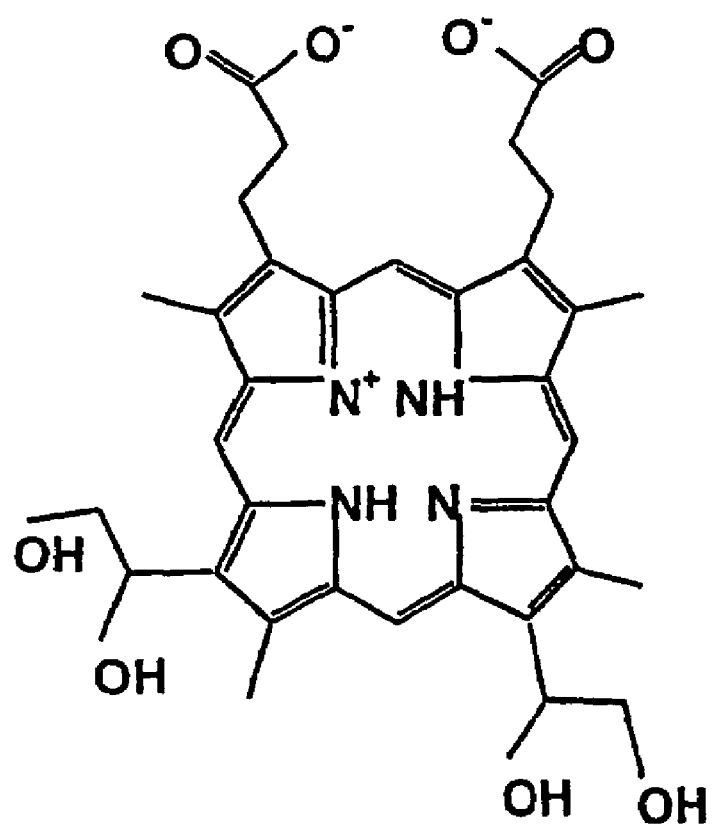
Figure 10E:
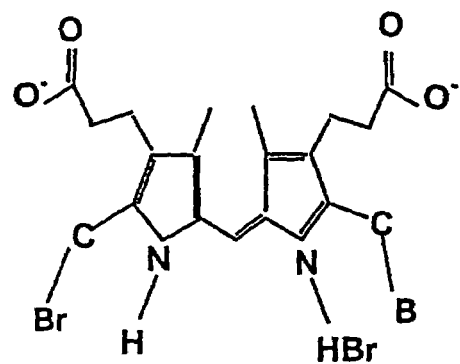
Figure 10F:
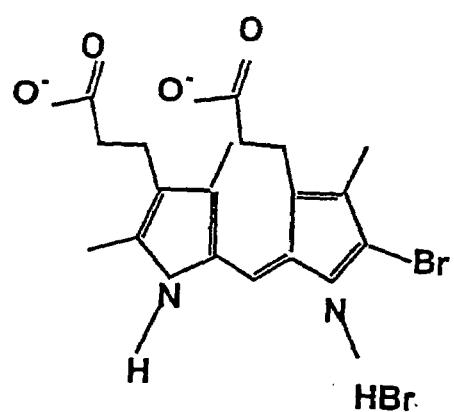
Figure 10G:
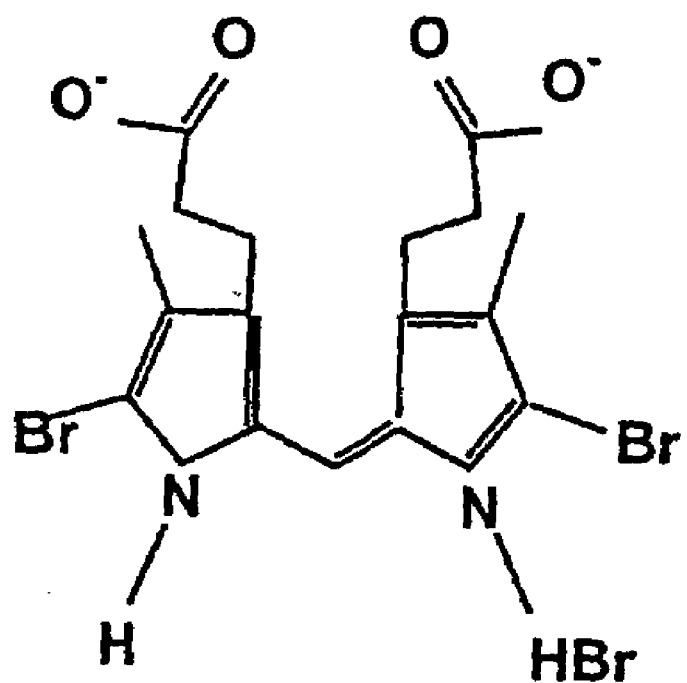
Figure 11A:
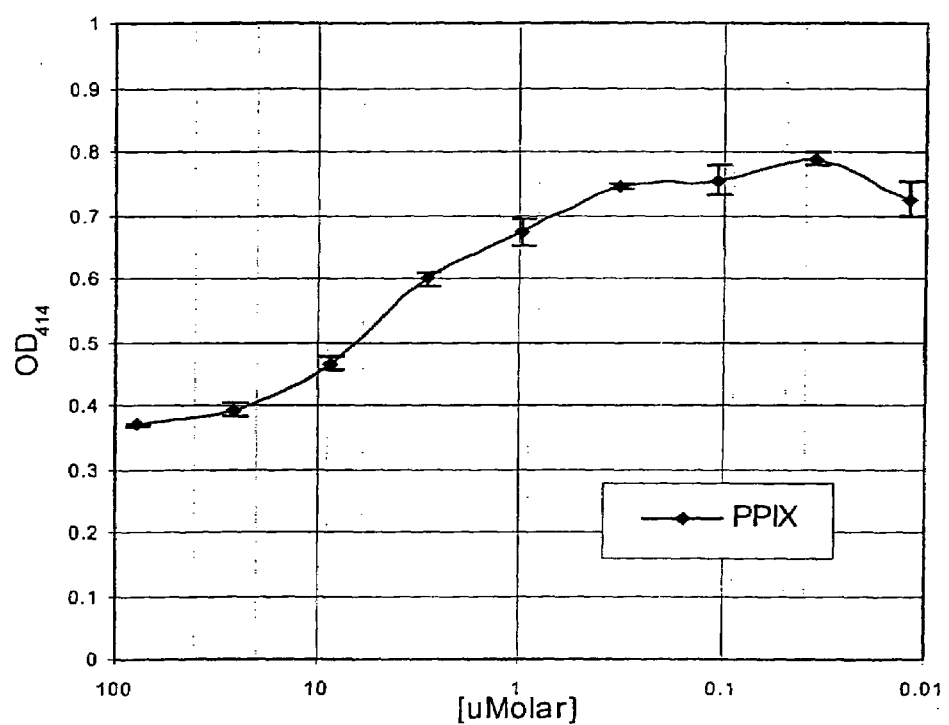
FIGS. 11a, 11b, 11c, 11d, 11e, 11f and 11g are graphical representations of showing competition between a ligand and hemoglobulin (HG) for rHA2 binding. The ligands employed were: (a) protoporphyrin 1X (PPIX); (b) deuteroporphyrin 1X 2,4 dihydrochloride (DDH); (c) deuteroporphyrin 1X 2,4 disulfonic acid (DDS); (d) deuteroporphyrin 1X 2,4 bisethylene glycol (DBEG); (e) dipyrrole 1 (C1; see FIG. 10); (f) dipyrrole 2 (C2; see FIG. 10) and (g) dipyrrole 3 (C3, see FIG. 10).
Figure 11B:
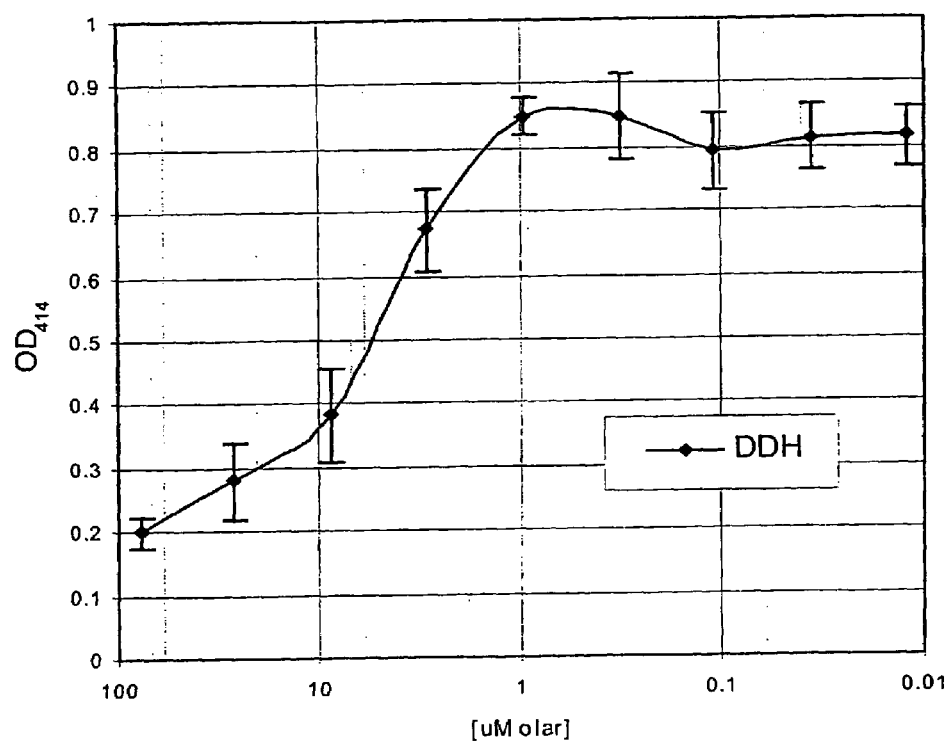
Figure 11C:
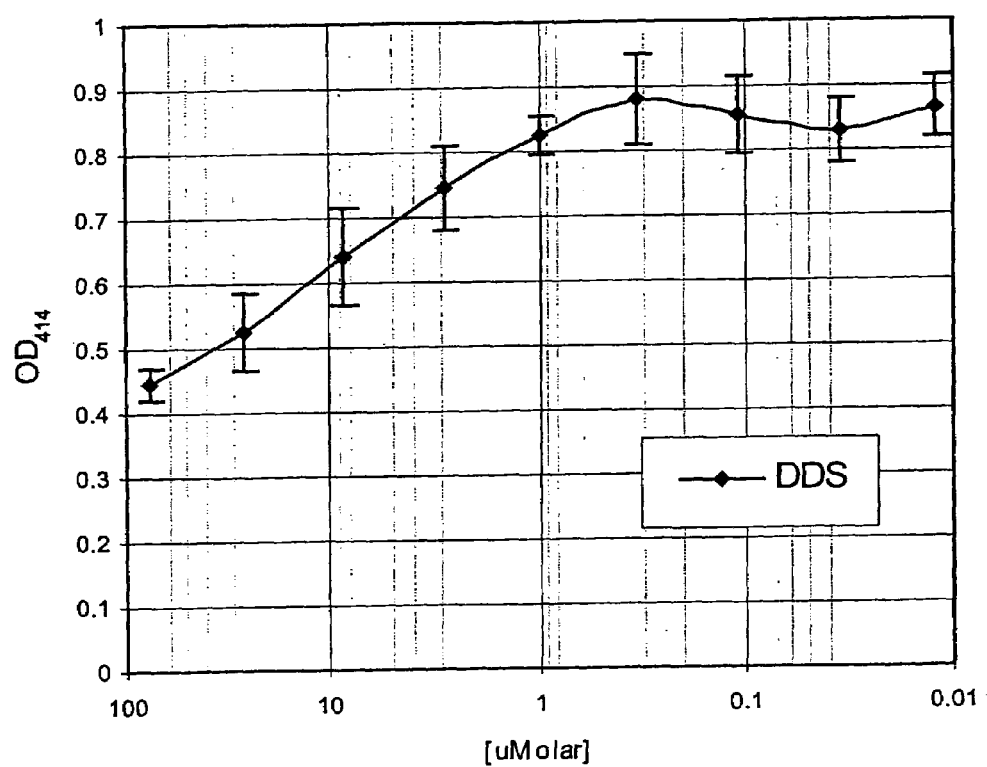
Figure 11D:
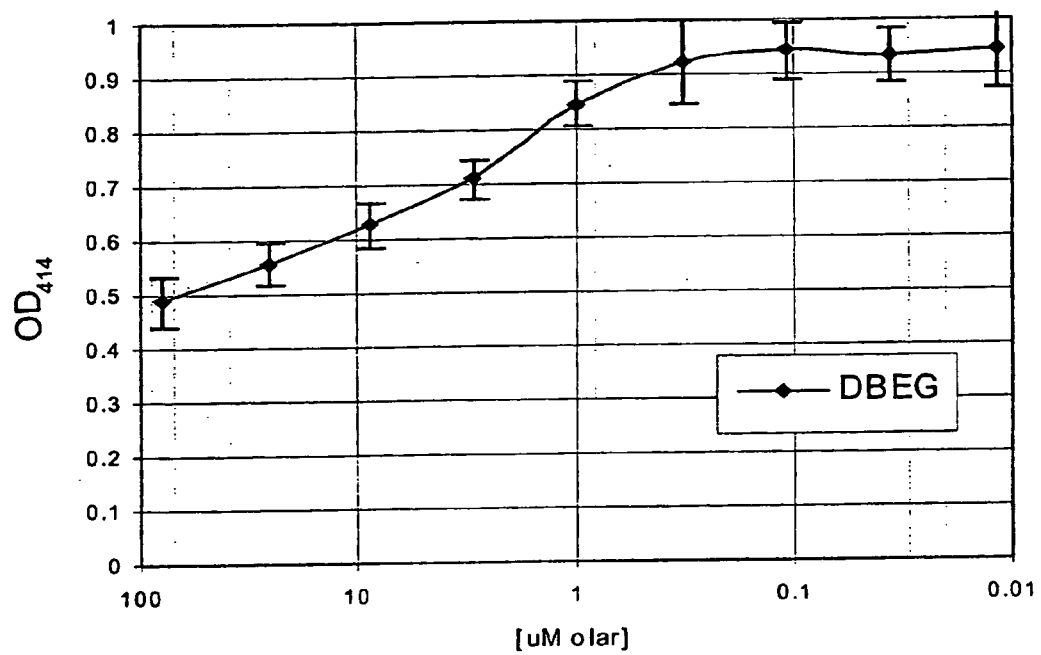
Figure 11E:
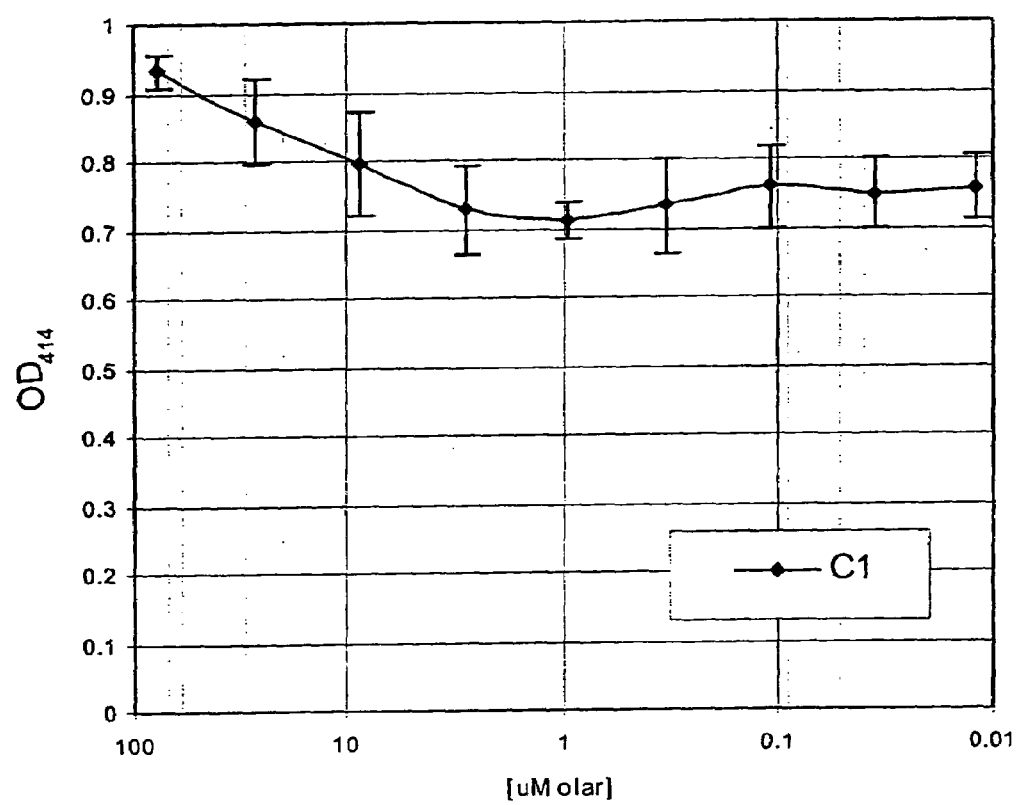
Figure 11F:
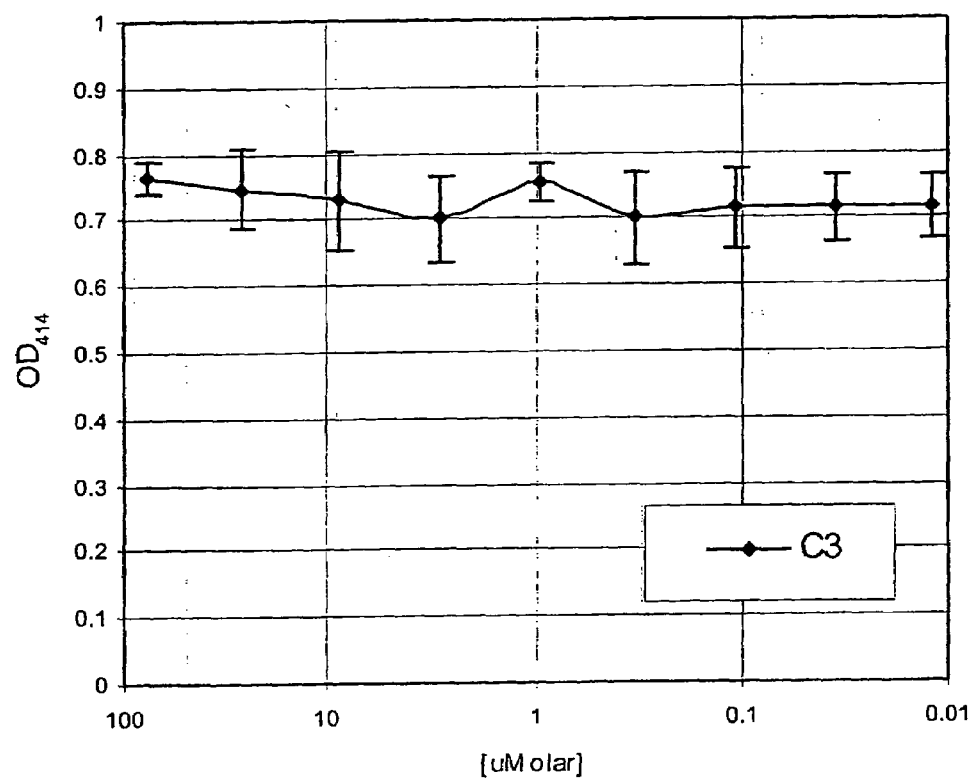
Figure 11G:
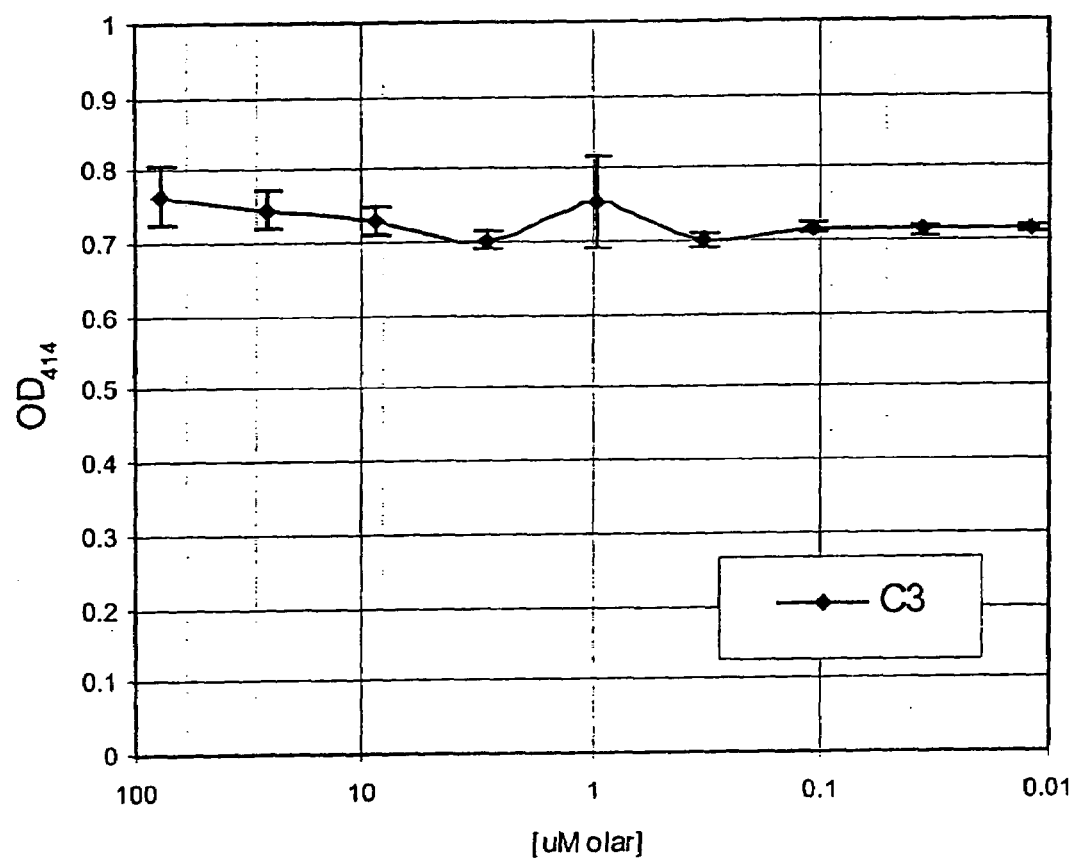

Immunoreactive protein in the cell-free conditioned culture medium detected with mAb 5A1 steadily accumulated throughout the 8 day culture period similar to proteolytic activity (FIG. 8c, open squares). Immunoreactive protein associated with hemoglobin-binding in this supernatant fraction also increased steadily throughout the extended culture in a parallel manner (FIG. 8c, closed squares). In the cellular fraction of the *P. gingivalis* culture, expression of immunoreactive protein increased early during the culture period with a peak near day 3 followed by a slight decrease then an increase to peak levels again by day 7, similar to proteolytic activity of this fraction (FIG. 8c, open triangles). Immunoreactive protein associated with hemoglobin-binding in the cellular fraction followed a parallel pattern of expression (FIG. 8c, closed triangles). These data demonstrated that detection of protein immunoreactive with mAb 5A1 in crude cellular and extra-cellular fractions of *P. gingivalis* culture was directly associated with hemoglobin-binding suggesting that mAb 5A1 specifically recognized the hemoglobin-binding, HA2 domain within *P. gingivalis* culture. Also, the data demonstrated a profile of HA2 domain expression and hemoglobin-binding activity similar with profiles of cellular and extra-cellular proteolytic activity expressed by *P. gingivalis*.

EXAMPLE 20

Controlling *Porphyromonas gingivalis* Growth

The control of *P. gingivalis* growth with prevention of periodontal pathology is achieved by interfering one or more pathways for obtaining heme. To this end, the inventors have shown that a monoclonal antibody recognizes an epitope within the hemoglobin-binding domain of the abundant *P. gingivalis* cysteine proteinases, i.e. gingipains, and have demonstrated increasing levels of this HA2 domain associated with hemoglobin-binding and proteinase activity in extended *P. gingivalis* culture. Further, the inventors have characterized the binding between the HA2 domain and hemoglobin suggesting that binding is mediated in large part through a specific recognition of the porphyrin ring of the heme moiety within the hemoglobin.

Characterization of the binding between the recombinant HA2 (rHA2) domain and porphyrins allows for the design of efficient affinity ligands for purifying HA2, and allow structure-based design for heme/hemoglobin binding inhibitors. Heme acquisition is considered fundamental to the growth of *P. gingivalis*, and intervention with specific agents to disrupt pathways for heme-binding or uptake allows the control or prevention of periodontal disease.

EXAMPLE 21

*Porphyromonas gingivalis* does not Contain a Functional Porphyrin-Biosynthetic Pathway The presence or absence of genetic sequences encoding enzymes required for porphyrin biosynthesis was assessed in *P. gingivalis*.

All entries for proteins used in the porphyrin biosynthesis pathway that are listed in the Swiss-Prot database (Release 37.0) were searched with TBlastN against the available genomic data for the *P. gingivalis* genome (45). This search comprised 257 eukaryotic, archaeal and prokaryotic protein sequences used in different pathways related to porphyrin biosynthesis. These are the standard enzymes in porphyrin biosythesis, alternative enzymes used by subsets of organisms, the enzymes of the $C_4$ and $C_5$ pathways for 5-aminolevinulic acid synthesis, and enzymes used in Vitamin $B_{12}$ synthesis. Preliminary sequence data for *P. gingivalis* was obtained from The Institute of Genomic Research through the website at www.tigr.org.

Open reading frames with some identity to enzymes required for heme synthesis were further examined by comparison with enzymes from four reference organisms: *Escherichia coli*, *Bacillus subtilis*, *Synechocystis* and *Aquifex aeolicus*, and the enzyme 5-aminolevulinic acid synthase from *Bradyrhizobium japonicum*. Open reading frames were identified using the program Map and translated with Translate (46). Sequence identity between protein sequences was calculated using the program GAP and multiple alignments performed with PileUp (46)

Enzymes used solely in the pathway for vitamin $B_{12}$ synthesis were reported as a match if there was an open reading frame (ORF) which has a BLAST score greater than 100. Enzymes and proteins involved in cytochrome synthesis were also BLAST searched against the genome. Proteins were aligned and identity calculated using GAP (46).

The proteins identified in Table 2 were BLAST searched against the *P. gingivalis* genome. No significant matches were detected for the proteins glutamyl-tRNA reductase, porphobilinogen synthase, porphobilinogen deaminase, uroporphyrinogen III cosynthase, uroporphyrinogen decarboxylase, coproporphyrinogen III oxidase, HemM or uroporphyrinogen III methylase.

The above observations indicate that *P. gingivalis* is unable to undergo de novo synthesis of porphyrin. Accordingly, the early and essential steps for synthesis of the tetrapyrrole ring are not encoded in the genome of *P. gingivalis*. As this organism has several proteins associated with tetrapyrrole rings, it is concluded that *P. gingivalis* has a requirement for porphyrin.

Table 2

Enzymes Used in Heme Biosynthesis

TABLE 2

Enzymes used in heme biosynthesis

| Enzyme | Function |
|---|---|
| Hem1/Hem0/HemA | 5-Aminolevulinic acid synthase |
| HemA/Hem1 | Glutamyl-tRNA reductase |
| HemB/Hem2 | Porphobilinogen synthase |
| HemC/Hem3 | Porphobilinogen deaminase |
| HemD/CysG/NasF | Uroporphyrinogen III cosynthase |
| HemE/DcuP | Uroporphyrinogen decarboxylase |
| HemF/Hem6 | Copropporhyrinogen III oxidase |
| HemH/HemZ | Ferrochelatase |
| HemL/HemK | Glutamate-1-semialdehyde 2, 1 aminotransferase |
| HemM | An enzyme in main pathway of synthesis of 5-aminolevulinate, possibly glutamyl-tRNA dehydrogenase |
| HemN | Oxygen-independent coproporphyrinogen III oxidase |
| HemX | Uroporphyrinogen III methylase |

TABLE 2-continued

Enzymes used in heme biosynthesis

| Enzyme | Function |
|---|---|
| HemX | Protoporphrinogen oxidase |
| GltX | Glutamyl-tRNA synthetase |

EXAMPLE 22

Clinical Studies

Patients presenting to a dental hospital were selected for a clinical study. The inclusion criteria were some level of adult periodontitis, no professional periodontal treatment within the prior three years nor use of antibiotics within the prior six months. Two donor sites, one relatively healthy and one with relatively advanced periodontal disease were selected in each mouth on the basis of radiographic examination. Clinical parameters were measured and plaque samples were obtained from each site. All periodontal samples and measurements were obtained by one of the inventors. Venous blood was collected within 30 min after plaque samples were obtained. Differences between categories were established by Student's 2-tailed t-test using 95% confidence levels. The relationships of values between categories were established by linear regression with a 95% confidence level. Levels of periodontal dizease severity were assigned the following values: 0, none; 1, localized mild; 2, generalized mild; 3, localized moderate; 4, generalized moderate; 5, localized severe; 6, generalized severe.

Predictors of periodontal disease diagnosis such as pocket depths in sites of advanced disease, inflammation levels and attachment loss were relevant in this study (Pearson's correlation, P=0.038, P=0.017, P<0.001, respectively).

The presence of the HA2 was defined by detection with the HA2-specific antibody mAb 5A1. Subgingival plaque samples collected from patients presenting for the first time for dental treatment were heat-denatured to maximize exposure of the HA2 domain and the epitope of mAb 5A1. Detection of the denatured HA2 domain with mAb 5A1 in plaque samples were more frequent in the relatively diseased donor sites than in the healthier donor sites (Student's t-test, P=0.004). HA2 levels were positively associated with inflammation at the corresponding sites (linear regression, P=0.046). The levels of HA2 were also strongly and positively associated with the amount of hemoglobin-binding activity that was measured from matched but non-denatured aliquots of these plaque samples (Pearsons' correlation, P<0.001).

The levels of the HA2 domain and levels of hemoglobin-binding activity measured in plaque samples from sites in the mouth were each positively associated with titres of serum IgG antibody specific for the rHA2 domain at the time of initial presentation (P<0.001, P=0.007, respectively). These data could be interpreted to indicate that lower HA2 levels in plaque and that either would predict lower HA2-specific IgG serum antibody levels in the patients at the time of presentation. These data suggest that the HA2 domain is immunogenic in a human population eliciting a humoral IgG response in proportion to antigenic load.

Pre-therapy titres of serum antibody specific for the rHA2 domain (IgM, IgA and IgG combined) were found to be negatively correlated with the amount of lost tooth support (attachment loss) at sites of advanced periodontitis (Pearson's correlation, P=0.33). Pre-therapy antibody against HA2 domain was predominantly of the IgM isotype (Student's t-test, P<0.02). Because loss of attachment is the greatest contributing factor in determining periodontal diagnosis and attachment loss was strongly correlated with periodontal diagnosis in this study (Pearson's correlation, P<0.001), these data suggest that a lower serum antibody response to the HA2 domain would predict a greater level of clinical periodontal disease at the time of presentation. Conversely, the interpretation could be made that increasing the anti-HA2 antibody levels would be to protect against periodontal disease destruction.

Second samples of sera were collected some time after the commencement of periodontal therapy to examine the possible inoculating effect that periodontal therapy might have on the host immune system. The commencement of treatment was significantly associated with an increase in IgG titre against the HA2 domain (Student's t-test, P<0.017) with no change in the IgM or IgA titres. Correspondingly, pre-therapy and post-therapy anti-rHA2 IgG titres in patients were positively correlated (P<0.001). Also, levels of HA2 domain in plaque at the time of initial presentation were positively correlated with post-therapy rHA2-specific IgG titres (P 0.1). These data strengthen evidence that the HA2 domain is immunogenic in a human population.

Importantly, serum antibody titres against the HA2 domain were correlated with serum antibody titres against the whole *P. gingivalis* organism (Pearson's correlation, P=002) implicating the HA2 domain as a significant extracellular antigenic constitutent of *P. gingivalis* and a good candidate for immunologic targeting.

After the initiation of periodontal therapy, capacity for neutralization of hemoglobin-binding of the gingipains with IgG from post-treatment sera had become negatively associated with the diagnosis of periodontal disease severity (linear regression, RgpA, P=0.33; Kgp, P=0.032). Neutralization of hemoglobin-binding activity was confirmed to be IgG dependent by removing the neutralizing capacity of IgG fractions with a second pass over a protein-G affinity column. Taken together, these data suggest that a capacity to develop higher IgG titres against the HA2 domain of the ginigpains may be associated with an increased functional antibody response in terms of hemoglobin-binding activity and protection against periodontal disease destruction.

EXAMPLE 23

Establishment of Principles of Porphyrin Interaction

In the solid-phase ligand-binding assay, rHA2 bound to the porphyrins with similar binding affinities (FIG. 9) showing that rHA2 was capable of binding to the propionic acid chains despite modification on the vinyl aspect. All the porphyrins tested were modified at the vinyl end to different degrees and the dipyrroles were half porphyrins with no vinyl moieties. The structures are shown in FIG. 10. Despite these differences they all exhibited similar apparent $K_d$s of between 5-20 nM.

In the competition assay, only the dipyrroles were shown not to compete with hemoglobin for rHA2 (FIG. 11). The apparent $IC_{50}$s for the deuteroporphyrins were again similar in value ranging from 3-8 μM (FIG. 11). This indicates that modification of the vinyl aspect did not affect the capacity of the porphyrins to compete for rHA2 as the $IC_{50}$s were comparable to that of protoporphyrin (PPIX). Of interest, the dipyrroles were incapable of competing with hemoglobin for rHA2 although they were capable of binding to rHA2 in the solid-phase assays. This is consistent with the non-planarity of free dipyrroles which is predictable based on their chemical structures. However, when bound to the plate, the dipyrroles are likely to be restrained and hence may present a propionic face as if were aligned in a plane. This implies that the planarity of the propionic face is important for effective competitive binding.

These results establish the key principles of the HA2 porphyrin interaction. These principles are necessary to guide the development of molecules that will compete efficiently in vivo for the HA2 moiety.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Page, R. C. (1998) *Ann. Periodontol.* 3:108-120
1a. Beck et al. (1998) *Ann. Periodontol.* 3:127-141
2. Dzink et al. (1988) *J. Clin. Periodontol.* 15: 316-323
2a. Albandar et al. (1997) *J. Periodontol.* 68:973-981.
3. Evans et al. (1992) *Arch. Oral Biol.* 37: 813-9
4. Fiehn et al. (1992) *J. Periodont. Res.* 27: 609-14
5. Hanazawa et al. (1991) *Infect. Immun.* 59: 1972-7
6. Malek et al. (1994) *J. Bacteriol.* 176:1052-9
7. Eke et al. (1989) *J. Med. Microb.* 28: 5-8
8. Touw et al. (1982) *Antonie Van Leeuwenhoek.* 48: 315-25
9. Hanazawa et al. (1985) *Infect. Immun.* 50:262-270
10. Sismey-Durrant, H. J. and Hopp, R. M. (1991) *Oral Microbiol. Immunol.* 6:378-80
11. Bedi, G. S. and Williams, T. (1994) *J. Biol. Chem.* 269:599-606
12. McDermid et al. (1988) *Infect. Immun.* 56:1096-100
13. DeCarlo et al. (1998) *J. Periodont. Res.* 33:408-420
14. DeCarlo et al. (1997) *J. Dent. Res.* 76:1260-1270
15. Scott et al. (1993) *J. Biol. Chem.* 268:7935-42
16. Sorsa et al. (1992) *Infect. Immun.* 60:4491-4495
17. Larjava et al. (1987) *Scand. J. Dent. Res.* 95:308-14
18. Calkins et al. (1998) *J. Biol. Chem.* 273:6611-6614
19. Yun et al. (1999) *Infect. Immun.* 67:
20. Fletcher et al. (1997) *J. Periodont. Res.* 32:200-205
21. Sundqvist et al. (1988) *Oral Microbiol. Immunol.* 3:103-7
22. Wingrove et al. (1992) *J. Biol. Chem.* 267:18902-18907
23. Fishburn et al. (1991) *Oral Microbiol. Immunol.* 6:209-15
24. Sato et al. (1987) *Arch. Oral Biol.* 32:235-8
25. Imamura et al. (1994) *J. Clin. Invest.* 94:361-7
26. Imamura et al. (1997) *J. Biol. Chem.* 272:16062-16067
27. Lantz et al. (1991) *J. Bacteriol.* 173:4263-70
28. Nishikata, M. and Yoshimura, F. (1991) *Biochem. Biophys. Res. Comm.* 178:336-342
29. Shah, H. N. and Gharbia, S. E. (1989) *FEMS Microbiol. Lett.* 52:213-7
30. Pike et al. (1994) *J. Biol. Chem.* 269:406-11
31. Potempa et al. (1995) *Infect. Immun.* 63:1176-1182
32. Mikolajczyk-Pawlinska et al. (1998) *Biol. Chem.* 379:205-211
33. Rangarajan et al. (1997) Mol. Microbiol. 23:955-965
34. DeCarlo, A. A. and Harber, G. J. (1997) *Oral Microbiol. Immunol.* 12:47-56
35. Fujimura, S, and Nakamura, T. (1989) *Oral Microbiol. Immunol.* 4:227-9
36. Grenier, D. and Mayrand, D. (1987) *Infect. Immun.* 55:111-7
37. Slakeski et al. (1998) *Microbiology.* 144:1583-1592
38. Nakayama et al. (1998) *Mol. Microbiol.* 27:51-61
39. Laemmli, U. K. (1970) *Nature* 227:680-685
40. Towbin et al. (1979) *Proc. Natl. Acad. Sci. USA.* 76:4350-4354
41. Eley, B. M. and Cox, S. W. (1996) *J. Periodontol.* 67:703-716
42. Qiu et al. (1996) *J. Immunol.* 156:3350-3356
43. Needleman and Wunsch (1970) *J. Mol. Biol.* 48: 43-453
44. Aduse-opoku et al. (1997) *J. Bacteriol.* 179:4778-4788.
45. Altschul et al. (1990) *J. Mol. Biol.* 215:403-10.
46. Genetics Computer Group, Inc. (1995) Program Manual for the Wisconsin Package, Version 8.1. 575 Science Drive, Madison, Wis., USA 53711.
47. Altschul et al. (1997) *Nuc. Acids Res.* 25:3389.
48. Ausubel et al., "Current Protocols in Molecular Biology" John Wiley & Sons Inc, 1994-1998, Chapter 15.
49. Bonner and Laskey (1974) *Eur. J. Biochem.* 46:83.
50. Marmur and Doty (1962) J. Mol. Biol. 5:109.
51. DeCarlo et al. (1999) *J. Bact.* 181:3784-3791
52. Haffajee, A. D. and Socransky, S. S. (1994) *Periodontology* 20005: 78-111.
53. Norris, J. M. and Love, D. N. (1995) *Clin. Infect. Dis.* 20(*Suppl.* 2): s314-6.
54. Holt et al. (1988) *Science* 239: 55-57.
55. Yun et al. (1999) *Infect. Immuno.* 67: 2986-95.
56. Smalley et al. (1998) *Biochem. J.* 331; 681-685.
57. Argos, P. (1987) *J. Mol. Biol.* 193: 385-396
58. Dayhoff, M. O. (1978) *Atlas of Protein Sequence and Structure* 5(3) National Biomedical Research Foundation (Washington, D.C.).

The invention claimed is:

1. A method for the treatment of infection by a microorganism in a biological environment from where the microorganism acquires iron, heme or porphyrin said method comprising administering to said environment an effective amount of an agent for a time and under conditions sufficient to antagonize the interaction between a molecule derived from said microorganism having an HA2 domain and an HA2-binding motif on a porphyrin containing molecule present in said biological environment, wherein the agent antagonizes the interaction between the molecule derived from said microorganism having the HA2 domain and the HA2-binding motif on the porphyrin containing molecule by specifically binding to one or both of (a) the HA2 domain of the molecule, and (b) the HA2-binding motif on the porphyrin containing molecule.

2. A method according to claim 1 wherein the microorganism is *Porphyromonas gingivalis* or a related microorganism.

3. A method according to claim 1 wherein the biological environment is a mammal or reptile or insect or bird or species of fish.

4. A method according to claim 3 wherein the mammal is a primate, human, livestock animal or a companion animal.

5. A method according to any one of claims 1 to 4 when used for the treatment of a disease condition in the oral cavity, nasopharynx, oropharynx, vagina or urethra or other vascular or mucosal regions or cavities or in the hooves of livestock animals.

6. A method according to any one of claims 1 to 4 wherein the HA2-containing molecule is a gingipain, an hagA gene product or a TonB-dependent protein.

7. A method according to claim 1 wherein the porphyrin moiety is a heme.

8. A method according to claim 7 wherein the HA2-binding motif comprises a region comprising or within substructure (Ic) of structure (I):

(I)

wherein $R_1$ and $R_6$ are the same or different and each is an alkyl such as a methyl, ethyl or propyl group, or hydrogen, hydroxyl, carboxyl, aldehyde, acetaldehyde or keto group, M is a metal ion in various oxidation states and is optionally present such that n is 0 or 1 or a structurally or functional homologue thereof.

9. The method according to claim 1 wherein said HA2 domain comprises:

(i) the amino acid sequence encoded by the nucleotide sequence set forth in SEQ ID NO:5 or a nucleotide sequence having at least 95% identity thereto or capable of hybridizing thereto under high stringency conditions of 0.1×SSC, and 0.1% w/v SDS at 65° C.; and/or (ii) the amino acid sequence as set forth in SEQ ID NO:6 or an amino acid sequence having at least 95% similarity thereto.

10. A method for treatment of periodontal, pulmonary, vaginal, urethral or hoof disease resulting from infection by *P. gingivalis* or related microorganism in a mammal said method comprising administering to said mammal an effective amount of a agent for a time and under conditions sufficient to antagonize the interaction between a *P. gingivalis*-derived molecule having an HA2 domain and an HA2-binding motif on hemoglobin, wherein the agent antagonizes the interaction between the *P. gingivalis*-derived molecule having the HA2 domain and the HA2-binding motif on the hemoglobin by specifically binding to one or both of (a) the HA2 domain of the *P. gingivalis*-derived molecule, and (b) the HA2-binding motif on the hemoglobin.

11. A method for the treatment of *P. gingivalis* infection or infection by a related microorganism in a mammal, said method comprising administering to said mammal an effective amount of an agent for a time and under conditions sufficient to antagonize the interaction between a *P. gingivalis*-derived HA2-containing molecule comprising the amino acid sequence ALNPDNYLISKDVTG (SEQ ID NO:1) or ALNPDNYLISKDVTGATKVKY (SEQ ID NO:8) or an amino acid sequence having at least 95% similarity to SEQ ID NO:1 or SEQ ID NO:8 after optimum after optimal alignment with the same sequence or the amino acid sequence encoded by the nucleotide sequence of SEQ ID NO:7 or a nucleotide sequence having at least 95% identity thereto or a nucleotide sequence capable of hybridizing thereto under high stringency conditions of 0.1×SSC, and 0.1% w/v SDS at 65° C. and an HA2-binding motif comprising propionic acid groups or anionic or salt forms thereof, wherein the agent antagonizes the interaction between the *P. gingivalis*-derived HA2-containing molecule and the HA2-binding motif by specifically binding to one or both of (a) the HA2 domain of the *P. gingivalis*-derived molecule, and (b) the HA2-binding motif.

12. A method according to claim 5 wherein the HA2-containing molecule is a gingipain, an hagA gene product or a TonB-dependent protein.

13. A method according to claim 6 wherein the porphyrin moiety is a heme.

14. A method according to claim 6, wherein the TonB-dependent protein is a Tla protein.

15. A method according to claim 8, wherein the metal ion M in various oxidation states is selected from the group consisting of Fe, $Fe^{++}$ and $Fe^{+++}$.

16. A method according to claim 9, wherein the molecule derived from said microorganism and having an HA2 domain and an HA2-binding moiety on a porphyrin-containing molecule is hemoglobin or a heme.

17. A method according to claim 11, wherein the HA2-binding motif comprising and including propionic acid groups or anionic or salt forms thereof is defined by substructure (Ic) in Formula (I) on a porphyrin-containing molecule.

18. A method according to claim 17, wherein the porphyrin-containing molecule is hemoglobin or a heme.

* * * * *